US009447011B2

(12) United States Patent
Ye et al.

(10) Patent No.: US 9,447,011 B2
(45) Date of Patent: Sep. 20, 2016

(54) METHODS, SYSTEMS AND DEVICES FOR SIMULTANEOUS PRODUCTION OF LACTIC ACID AND PROPYLENE GLYCOL FROM GLYCEROL

(71) Applicant: University of Tennessee Research Foundation, Knoxville, TN (US)

(72) Inventors: Xiaofei Philip Ye, Knoxville, TN (US); Lu Liu, Knoxville, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 14/646,670

(22) PCT Filed: Nov. 21, 2013

(86) PCT No.: PCT/US2013/071279
§ 371 (c)(1),
(2) Date: May 21, 2015

(87) PCT Pub. No.: WO2014/081951
PCT Pub. Date: May 30, 2014

(65) Prior Publication Data
US 2015/0299082 A1    Oct. 22, 2015

Related U.S. Application Data

(60) Provisional application No. 61/729,181, filed on Nov. 21, 2012.

(51) Int. Cl.
| | | |
|---|---|---|
| *C07C 51/00* | (2006.01) | |
| *C07C 29/00* | (2006.01) | |
| *B01J 23/86* | (2006.01) | |
| *B01J 23/78* | (2006.01) | |
| *B01J 23/72* | (2006.01) | |
| *B01J 19/24* | (2006.01) | |
| *C07C 51/347* | (2006.01) | |
| *C07C 51/50* | (2006.01) | |
| *C07C 59/08* | (2006.01) | |
| *B01J 38/02* | (2006.01) | |
| *B01J 23/94* | (2006.01) | |
| *C07C 29/32* | (2006.01) | |

(52) U.S. Cl.
CPC ............... *C07C 51/00* (2013.01); *B01J 19/24* (2013.01); *B01J 23/72* (2013.01); *B01J 23/78* (2013.01); *B01J 23/868* (2013.01); *B01J 23/94* (2013.01); *B01J 38/02* (2013.01); *C07C 29/00* (2013.01); *C07C 29/32* (2013.01); *C07C 51/347* (2013.01); *C07C 51/50* (2013.01); *C07C 59/08* (2013.01); *B01J 2219/24* (2013.01); *Y02P 20/584* (2015.11)

(58) Field of Classification Search
CPC ..... C07C 51/00; C07C 51/347; C07C 51/50; C07C 29/32; C07C 29/00; C07C 59/08; B01J 23/78; B01J 23/94; B01J 23/72; B01J 23/868; B01J 19/24; B01J 38/02; B01J 2219/24; Y02P 20/584

See application file for complete search history.

(56) References Cited

U.S. PATENT DOCUMENTS

| | | | |
|---|---|---|---|
| 5,210,296 A | 5/1993 | Cockrem et al. | |
| 8,563,783 B2 * | 10/2013 | Suppes ................ | C07C 29/145 568/861 |
| 2008/0103339 A1 | 5/2008 | Bloom | |
| 2008/0228014 A1 | 9/2008 | Bloom | |
| 2008/0242898 A1 | 10/2008 | Miller et al. | |
| 2009/0264686 A1 | 10/2009 | Holladay et al. | |
| 2010/0137654 A1 | 6/2010 | Bricker | |
| 2010/0160691 A1 | 6/2010 | Bricker et al. | |
| 2010/0179346 A1 | 7/2010 | Klein et al. | |
| 2011/0207971 A1 | 8/2011 | Frye et al. | |
| 2011/0207972 A1 | 8/2011 | Brown et al. | |
| 2012/0253067 A1 | 10/2012 | Chaudhari et al. | |
| 2012/0296110 A1 | 11/2012 | Barve et al. | |
| 2013/0079547 A1 | 3/2013 | Yoon et al. | |

FOREIGN PATENT DOCUMENTS

| | | |
|---|---|---|
| CN | 101214440 | 7/2008 |
| CN | 101225041 | 7/2008 |
| CN | 101380576 | 3/2009 |
| CN | 101381280 | 3/2009 |
| CN | 101422739 | 5/2009 |
| CN | 101428222 | 5/2009 |
| CN | 101497047 | 8/2009 |

(Continued)

OTHER PUBLICATIONS

Chen, "Conversion of glycerol to lactic acid under low corrosive conditions with homogeneous and heterogeneous catalysts," Masters Thesis, University of Tennesse, Knoxville, 2011; http://trace.tennessee.edu/UTK_gradthes/960.

He et al., "Application of hydrothermal reaction in resouce recovery of organic wastes," Resources, Conservation and Recycling, vol. 52 pp. 691-699 (2008).

Hongo et al., "Novel method of lactic-acid production by electrodialysis fermentation," Applied and Environmental Microbiology, vol. 52, No. 2 pp. 314-319 (1986).

Kim et al., "Effect of recycle and feeding method on batch reactive recovery system of lactic acid," Korean Journal of Chemical Engineering, vol. 19, No. 5 pp. 808-814 (2002).

(Continued)

*Primary Examiner* — Shailendra Kumar
(74) *Attorney, Agent, or Firm* — Jenkins, Wilson, Taylor & Hunt, P.A.

(57) ABSTRACT

Methods, processes and systems for using solid catalysts to simultaneously produce lactic acid and propylene glycol from glycerol are provide, as are methods, processes and systems of converting glycerol use heterogeneous catalytic agents. Different combinations of catalysts and reaction conditions provide tunable ranges for the yields of lactic acid and propylene glycol. The conversion methods, processes and systems are not reliant on external hydrogen. Applications to crude glycerol, including that co-produced during biodiesel production, are also described.

25 Claims, 12 Drawing Sheets

(56) References Cited

FOREIGN PATENT DOCUMENTS

| | | |
|---|---|---|
| CN | 101628871 | 1/2010 |
| CN | 101767006 | 7/2010 |
| CN | 101898946 | 12/2010 |
| CN | 102153446 | 8/2011 |
| CN | 102173977 | 9/2011 |
| CN | 102225883 | 10/2011 |
| EP | 2298720 | 3/2011 |
| JP | 2008044874 | 2/2008 |
| JP | 2008143798 | 6/2008 |
| JP | 2009173550 | 8/2009 |
| JP | 2009179594 | 8/2009 |
| JP | 2010111618 | 5/2010 |
| JP | 4906720 | 3/2012 |
| WO | WO2008/049470 | 5/2008 |
| WO | WO2009/096134 | 8/2009 |
| WO | WO2009/145691 | 12/2009 |
| WO | WO2009/149830 | 12/2009 |
| WO | WO2010/074954 | 7/2010 |
| WO | WO2010/102361 | 9/2010 |
| WO | WO2010/150278 | 12/2010 |
| WO | WO2011/104634 | 9/2011 |
| WO | WO2011/106046 | 9/2011 |
| WO | WO2011/106048 | 9/2011 |
| WO | WO 2014/081951 | 5/2014 |

OTHER PUBLICATIONS

Long et al., "Production of biodiesel and lactic acid from rapeseed oil using sodium silicate as catalyst," Bioresouce Technology, vol. 102 pp. 6884-6886 (2011).

Notification Concerning Transmittal of International Preliminary Report on Patentability (Chapter I of the Patent Cooperation Treaty), corresponding to PCT/US2013/071279, mailed Jun. 4, 2015.

Notification of Transmittal of the International Search Report and The Written Opinion of the International Searching Authority, or the Declaration, corresponding to PCT/US2013/071279, mailed on Feb. 27, 2014.

Tang et al., "Highly active CaO for the transesterification to biodiesel," Bull. Chem. Soc. Ethiop., vol. 25 pp. 37-42 (2011).

Van Gerpen, "Biodiesel processing and production," Fuel Processing Technology, vol. 86, No. 10 pp. 1097-1107 (2005).

Viboonchart, "Kingdom to become lactic-acid hub," http://www.nationmultimedia.com/home/2010/04/01/business/Kingdom-to-become-lactic-acid-hum-30126072.html (accessed Dec. 2011).

Wang et al., "Conversion of triose sugars with alcohols to alkyl lactates catalysed by Bronsted acid tin ion-exchanged montmorillonite," Applied Catalysis B: Environmental, vol. 107, Nos. 1-2 pp. 135-139 (2011).

Werpy and Petersen, Top Value Added Chemicals from Biomass. Results of Screening for Potential Candidates from Sugars and Syntehsis Gas. The Pacific Northwest Laboratory, The National Renewable Energy Laboratory, U.S. Department of Energy, Office of Scientific and Technical Information (2004).

Auneau et al., "Heterogeneous transformation of glycerol to lactic acid," Topics in Catalysis, vol. 55, Nos. 7-10 pp. 474-479 (2012).

Barve et al., "Preparation of pure methyl esters from corresponding alkali metal salts of carboxylic acids using carbon dioxide and methanol," Industrial & Engineering Chemistry Research, vol. 51, No. 4 pp. 1498-1505 (2012).

Boyaval et al., "Continuous lactic-acid fermentation with concentrated product recovery by ultrafiltration and electrodialysis," Biotechnology Letters, vol. 9, No. 3 pp. 207-212 (1987).

Chiu et al., "Reducing byproduct formation during conversion of glycerol to propylene glycol," Industrial & Engineering Chemistry Research, vol. 47 pp. 6878-6884 (2008).

Chiu et al., "Removal of residual catalyst from simulated biodiesel's crude glycerol for glycerol hydrogenolysis to propylene glycol," Industrial & Engineering Chemistry Research, vol. 45 pp. 791-795 (2006).

Datta et al., "Technological and economic potential of poly(lactic acid) and lactic-acid derivatives," Fems Microbiology Revies, vol. 16, Nos. 2-3 pp. 221-231 (1995).

Dusselier et al., "Lactic acid as a platform chemical in the biobased economy: the role of chemocatalysis," Energy & Environmental Science, vol. 6, No. 5 pp. 1415-1442 (2013).

Feng et al., "Hydrogenolysis of glycerol to glycols over ruthenium catalysts: effect of support and catalyst reduction temperature," Catalysis Communications, vol. 9 pp. 1458-1464 (2008).

Granados et al., Biodiesel from sunflower oil by using activated calcium oxide, Applied Catalysis B: Environmental, vol. 73, Nos. 3-4, pp. 317-326 (2007).

Hao et al., "Hydrogenolysis of glycerol to 1,2-propanediol catalyzed by Cu—H(4)SiW(12)O(40)/Al(2)O(3) in liquid phase," Journal of Chemical Technolgy and Biotechnology, vol. 85 pp. 1499-1503 (2010).

Holm et al., "Conversion of sugars to lactic acid derivatives using heterogeneous zeotype catalysts," Science, vol. 328, No. 5978 pp. 602-605 (2010).

Huang et al., "Continuous production of 1,2-propanediol by the selective hydrgenolysis of solvent-free glycerol under mild conditions," Journal of Chemical Technology and Biotechnology, vol. 83 pp. 1670-1675 (2008).

Johnson and Taconi, "The glycerin glut: options for the value-added conversion of crude glycerol resulting from biodiesel production," Environmental Progress, vol. 26 pp. 338-348 (2007).

Kamble et al., "Purification of lactic acid via esterification of lactic acid using a packed column, followed by hydrolysis of methyl lactate using three continuously stirred tank reactors (CSTRs) in series: a continous pilot plant study," Industrial & Engineering Chemistry Research, vol. 51, No. 4 pp. 1506-1514 (2012).

Kim et al. "Effect of preparation method on structure and catalytic activity of Cr-promoted Cu catalyst in glycernol hydrogenolysis," Korean Journal of Chemical Engineering, vol. 27 pp. 431-434 (2010).

Kishida et al., "Conversion of glycerin into lactic acid by alkaline hydrothermal reaction," Chemistry Letters, vol. 34, No. 11 pp. 1560-1561 (2005).

Kouzu et al., "A process to transesterify vegetable oil with methanol in the presence of quick lime bit functioning as solid base catalyst," Fuel, vol. 88, No. 10 pp. 1983-1990 (2009).

Kouzu et al., "Active phase of calcium oxide used as solid base catalysts for transesterification of soybean oil with refluxing methanol," Applied Catalysis A: General, vol. 334, Nos. 1-2 pp. 357-365 (2008).

Kouzu et al., "Heterogeneous catalysis of calcium oxide used for transesterification of soybean oil with refluxing methanol," Applied Catalysis A: General, vol. 355, Nos. 1-2 pp. 94-99 (2009).

Kouzu, "Eco-friendly production of biodiesel by utilizing solid base catalysis of calcium oxide for reaction to convert vegetable oil into its methyl esters," pp. 20-28 in Zero Carbon Energy Kyoto 2009, Springer Japan (2010).

Kumar et al., "A continuous process for the recovery of lactic acid by reactive distillation," Journal of Chemical Technology and Biotechnology, vol. 81, No. 11 pp. 1767-1777 (2006).

Lahr and Shanks, "Effect of sulfur and temperature on ruthenium-catalyzed glycerol hydrogenolysis to glycols," Journal of Catalysis, vol. 232 pp. 386-394 (2005).

Lahr and Shanks, "Kinetic analysis of the hydrogenolysis of lower polyhydric alcohols: glycerol to glycols," Industrial & Engineering Chemistry Research, vol. 42 pp. 5467-5472 (2003).

Lee and Moon, "Studies on the conversion of glycerol to 1,2-propanediol over Ru-based batalyst under mild conditions," Catalysis Today, vol. 174 pp. 10-16 (2011).

Liu et al., "Conversion of biomass-derived carbohydrates to methyl lactate using solid base catalysts," Catalysis Communications, vol. 15, No. 1 pp. 82-87 (2011).

Liu et al., "Transesterification of soybean oil to biodiesel using CaO as a solid base catalyst," Fuel, vol. 87, No. 2 pp. 216-221 (2008).

Lux et al., "Lactic acid production as a new approach for exploitation of glycerol," Separation Science and Technology, vol. 45, pp. 1921-1927 (2010).

(56) References Cited

OTHER PUBLICATIONS

Ma et al., "Glycerol hydrogenolysis to propanediols over Ru—Re/SiO(2): acidity of catalyst and role of Re," Chinese Journal of Catalysis, vol. 32 pp. 872-876 (2010).

Maglinao and He, "Catalytic thermochemical conversion of glycerol to simple and polyhydric alcohols using raney nickel catalyst," Industrial & Engineering Chemistry Research, vol. 50 pp. 6028-6033 (2011).

Mane et al., "Role of promoters in copper chromite catalysts for hydrogenolysis of glycerol," Catalysis Today, vol. 164 pp. 447-450 (2010).

Maris and Davis, "Hydrogenolysis of glycerol over carbon-supported Ru and Pt catalysts," Journal of Catalysis, vol. 249 pp. 328-337 (2007).

Meher et al., "Catalytic hydrogenolysis of glycerol to propylene glycol over mixed oxides derived from a hydrotalcite-type precursor," Industrial & Engineering Chemistry Research, vol. 48 pp. 1840-1846 (2009).

Ngamcharussrivichai et al., "Ca and Zn mixed oxide as a heterogeneous base catalyst for transesterification of palm kernel oil," Applied Catalysis A: General, vol. 341, Nos. 1-2 pp. 77-85 (2008).

Panyad et al., "Catalytic dehydrosylation of glycerol to propylene glycol over Cu—ZnO/Al(2)O(3)catalysts: effects of catalyst preparation and deactivation," Catalysis Today, vol. 174 pp. 59-64 (2011).

Ramirez-Lopez et al., "Synthesis of lactic acid by alkaline hydrothermal conversion of glycerol at high glycerol concentration," Industrial & Engineering Chemistry Research, vol. 49, No. 14 pp. 6270-6278 (2010).

Roy et al., "Cu-based catalysts show low temperature activity for glycerol conversion of lactic acid," Acs Catalysis, vol. 1, No. 5 pp. 548-551 (2011).

Ruppert et al., "Glycerol etherification over highly active CaO-based materials: new mechanistic aspects and related colloidal particle formation," Chemistry-a European Journal, vol. 14 pp. 2016-2024 (2008).

Shen et al., "Effect of alkaline catalysts on hydrothermal conversion of glycerin into lactic acid," Industrial & Engineering Chemistry Research, vol. 48, No. 19 pp. 8920-8925 (2009).

Shen et al., "Efficient sysnthesis of lactic acid by aerobic oxidation of glycerol on Au—Pt/TiO2 catalysts," Chemistry-a European Journal, vol. 16 p. 7368-7371(2009).

Vijaykumar et al., "Recent trends in the production, purification and application of lactic acid," Chemical and Biochemical Engineering Quarterly, vol. 22, No. 2 pp. 245-264 (2008).

West et al., "Zeolite H-USY for the productionof lactic acid and methyl lactate from C3-sugars," Journal of Catalysis, vol. 269, No. 1 pp. 122-130 (2010).

Wolosiak-Hnat et al., "Influence of reduction time of copper-based catalysts: Cu/Al(2)O(3) and CuCr(2)O(4) on hydrogenolysis of glycerol," Polish Journal of Chemical Technology, vol. 13 pp. 71-76 (2011).

Xu et al., "Catalytic conversion of glycerin with NaOH under mild temperature," Electrical and Contorl Engineering (ICECE) pp. 1520-1525 (2010).

Yadav et al., "Hydrogenolysis of glycerol to 1,2-propanediol over nano-fibrous Ag—OMS-2 catalysts," Industrial & Engineering Chemistry Research, vol. 51 pp. 1549-1562 (2011).

Yuksel et al., "Hydrothermal electrolysis of glycerol using a continuous flow reactor," Industrial & Engineering Chemistry Research, vol. 49 pp. 1520-1525 (2010).

Zhao et al., "Catalytic dehydration-hydrogenation of glycerol to 1,2-propylene glycol at ambient hydrogen pressure," Chinese Journal of Catalysis, vol. 31 pp. 200-204 (2010).

\* cited by examiner

METHODS, SYSTEMS AND DEVICES FOR SIMULTANEOUS PRODUCTION OF LACTIC ACID AND PROPYLENE GLYCOL FROM GLYCEROL

RELATED APPLICATIONS

This application is a 371 of PCT/US2013/071279, filed on Nov. 21, 2013, which claims the benefit of U.S. Provisional Patent Application Ser. No. 61/729,181, filed Nov. 21, 2012; the disclosure of which is incorporated herein by reference in its entirety.

TECHNICAL FIELD

The presently disclosed subject matter relates generally to methods of converting glycerol to value-added products. In some embodiments, the presently disclosed subject matter relates to methods of simultaneously producing lactic acid and propylene glycol from glycerol.

BACKGROUND

Biodiesel production capacity worldwide is increasing every year with regulatory and socioeconomic motivations for renewable energy. One mole of glycerol is generated along with each mole of triglyceride converted to biodiesel. As the result of biodiesel growth, large amount of glycerol are produced and are available to the marketplace. Various sources [1, 2] have reported that the price of glycerol has been lowered by its large availability, and even credits are given for selling the crude glycerol. Development of value-added chemicals from glycerol, the co-product with biodiesel, is necessary to help sustain the biodiesel industry. Glycerol is listed among the 12 top building block chemicals from renewable biomass by the United States Department of Energy (DOE) [3].

Lactic acid (LA) has been viewed as a "commodity chemical sleeping giant", owing to its multiple reactive functionalities that make it readily convertible to other important commodity chemicals, such as ethyl lactate and poly(lactic acid). Currently, LA is primarily produced via fermentation of carbohydrates, which suffers from low productivity and efficiency and might not be sufficient to meet the increasing demand of LA in the chemical industry [4].

To date, almost all reported LA studies using chemical methods instead of biological methods of fermentation were conducted using homogeneous alkaline solutions; more specifically, good LA yields were achieved with homogeneous solution of either NaOH or KOH. High corrosiveness caused by NaOH and KOH under hydrothermal conditions constrained the allowable concentration of alkaline, and consequently concentration of glycerol in the reactants. This limitation negatively influences the productivity of LA. Furthermore, there is no inexpensive separation process to remove NaOH/KOH from the products, which hinders the promotion of industrialization of the technology. Moreover, most processes developed for glycerol-to-PG conversion require an external supply of hydrogen, which is associated with additional purchase and handling costs. Furthermore, depending on the hydrogen source, the developed PG process, which should ideally be based on renewable resources, could become dependent on fossil fuels. These problems have hindered and continue to hinder the commercialization of value-added chemicals from glycerol.

Thus, new methods, systems and devices for the conversion of glycerol to value-added components such as lactic acid and propylene glycol are needed.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments of the presently disclosed subject matter, a method of converting glycerol to lactic acid, propylene glycol or a combination thereof, is provided, the method comprising: providing liquid glycerol, providing a heterogeneous catalyst, and reacting the liquid glycerol with the heterogeneous catalyst, whereby glycerol is converted to a product comprising lactic acid, propylene glycol or a combination thereof. In some embodiments, reacting the liquid glycerol with the heterogeneous catalyst causes simultaneous production of lactic acid and propylene glycol. In some embodiments, the heterogeneous catalyst comprises a base ingredient and a dehydrogenation ingredient. In some embodiments, the dehydrogenation ingredient comprises a metal catalyst. In some embodiments, the metal catalyst is selected from the group consisting of copper (Cu), cuprous oxide ($Cu_2O$), copper oxide (CuO), copper chromite ($Cu_2Cr_2O_5$), barium promoted copper chromite (Ba—$Cu_2Cr_2O_5$) and copper ore. In some embodiments, the base ingredient comprises an alkaline earth metal. In some embodiments, the alkaline earth metal comprises an alkaline earth metal oxide selected from the group consisting of magnesium oxide (MgO), calcium oxide (CaO), and strontium oxide (SrO). In some embodiments, the base ingredient and dehydrogenation ingredient of the heterogeneous catalyst are mixed. In some embodiments, the heterogeneous catalyst mixture comprises CaO and $Cu_2O$. In some embodiments, the dehydrogenation ingredient is supported on the base ingredient. In some embodiments, the base supported dehydrogenation ingredient comprises $Cu_2O$ supported on CaO.

In some embodiments, the glycerol is concentrated glycerol. In some embodiments, the concentrated glycerol comprises glycerol with a purity of about 70% to about 100%. In some embodiments, the concentrated glycerol has a purity of 100%. In some embodiments, the concentrated glycerol has corrosiveness lower than that of crude glycerol. In some embodiments, the glycerol is crude glycerol, optionally wherein the crude glycerol comprises about 75% to about 85% glycerol and about 5% to about 15% water, optionally wherein the crude glycerol has a pH of about 6 to about 7. In some embodiments, the source of glycerol is biodiesel production.

In some embodiments, hydrogen is generated in-situ during the conversion of glycerol to lactic acid and propylene glycol. In some embodiments, no external hydrogen is required for the conversion of glycerol to lactic acid and propylene glycol.

In some embodiments, the lactic acid produced is racemic, optionally with a molar ratio of L-(+)-lactic acid to D-(−)-lactic acid of about 1. In some embodiments, the dehydrogenation ingredient is recoverable and optionally can be recycled in the method of converting glycerol to lactic acid and propylene glycol. In some embodiments, the efficiency of conversion of glycerol and the yield of lactic acid and propylene glycol is increased or decreased by one or more of the following factors: the concentration of water in the glycerol; the purity of the glycerol; or the pressure under which the reaction occurs.

In some embodiments, a method of converting glycerol as disclosed herein can further comprise providing a reaction tube and reacting the liquid glycerol with the heterogeneous catalyst. In some embodiments, the glycerol conversion ranges from about 70% to about 95%. In some embodiments, the lactic acid yield ranges from about 50% to about 70%. In some embodiments, the propylene glycol yield ranges from about 10% to about 40%. In some embodiments, the carbon balance ranges from about 75% to about 99%.

In some embodiments, the molar ratio of the dehydrogenation ingredient to glycerol ranges from about 0.02 to about 0.10. In some embodiments, the molar ratio of the dehydrogenation ingredient to glycerol is about 0.04 to about 0.08. In some embodiments, the molar ratio of the base ingredient to glycerol ranges from about 0.2 to about 0.8. In some embodiments, the molar ratio of the base ingredient to glycerol is about 0.4. In some embodiments, the molar ratio of the dehydrogenation ingredient to the base ingredient is about 1:2 to about 1:20.

In some embodiments, the reaction occurs at about 160° C. to about 270° C. for about 40 minutes to about 180 minutes. In some embodiments, the reaction occurs at about 190° C. for about 60 minutes.

In some embodiments, a method of converting glycerol as disclosed herein can further comprise regenerating spent catalyst, optionally wherein the spent catalyst comprises $Ca(OH)_2$ and Cu, optionally wherein the regeneration comprises a calcination process, optionally wherein the regenerated catalyst comprise CaO and CuO. In some embodiments, a method of converting glycerol as disclosed herein can further comprise using regenerated catalyst CaO and CuO in the glycerol conversion method. In some embodiments, the reaction occurs at about 230° C. to about 240° C. for about 60 minutes to about 180 minutes.

In some embodiments, provided herein is a method of converting glycerol to lactic acid and propylene glycol, the method comprising: providing a glycerol stock, providing a heterogeneous catalyst, wherein the heterogeneous catalyst comprises a base ingredient and a dehydrogenation ingredient, reacting the glycerol stock with the heterogeneous catalyst, cooling and washing the products of the reaction, wherein the products comprise lactate salt, glycerol and propylene glycol, treating the lactate salt with sulfuric acid solution to form free lactic acid and a sulfate salt, and separating the propylene glycol from the remaining products, whereby glycerol is converted to a lactic acid and propylene glycol.

In some embodiments, the lactic acid is concentrated to about 90% as final product in a distillation tower. In some embodiments, a method of converting glycerol can further comprise a two-phase distillation process to separate glycerol and propylene glycol. In some embodiments, a method of converting glycerol can further comprise regenerating spent catalyst, optionally wherein the spent catalyst comprises $Ca(OH)_2$ and Cu, optionally wherein the regeneration comprises a calcination process, optionally wherein the regenerated catalyst comprise CaO and CuO. In some embodiments, glycerol remaining after the reaction is recycled a glycerol stock in the method of converting glycerol to lactic acid and propylene glycol. In some embodiments, the dehydrogenation ingredient comprises a metal catalyst, and wherein the base ingredient comprises an alkaline earth metal.

Provided herein in some embodiments is a glycerol conversion system, comprising: a reactor for reacting stock glycerol with a heterogeneous catalyst, wherein the heterogeneous catalyst comprises a base ingredient and a dehydrogenation ingredient, a rotary vacuum filter for cooling and washing the products of the reaction in the reactor, optionally wherein a filtrate containing calcium lactate, glycerol and propylene glycol is separated from a filter cake containing Cu and $Ca(OH)_2$, a crystallizer for filtering out calcium lactate from the filtrate, wherein the calcium lactate is treated with sulfuric acid solution to form lactic acid, a distillation tower for concentrating lactic acid, and a series of separation towers for separating glycerol and propylene glycol from the filtrate.

In some embodiments, the reactor comprises a continuous stirred tank reactor. In some embodiments, the reactor comprises a reaction chamber for containing the reaction, optionally wherein the reaction chamber comprises a thermocouple, and optionally wherein the reaction chamber is submerged in an aqueous bath. In some embodiments, a reactor as disclosed herein can further comprise a furnace for calcinating Cu and $Ca(OH)_2$ in the filter cake to thereby form CuO and CaO, wherein CuO and CaO are recycled and used in the reactor as the dehydrogenation ingredient and base ingredient, respectively. In some embodiments, a reactor as disclosed herein can further comprise storage containers for storing the produced lactic acid and propylene glycol.

Accordingly, it is an object of the presently disclosed subject matter to provide new methods, systems and devices for the conversion of glycerol to value-added components such as lactic acid and propylene glycol. These objects are achieved in whole or in part by the presently disclosed subject matter.

An object of the presently disclosed subject matter having been stated hereinabove, and which is achieved in whole or in part by the presently disclosed subject matter, other objects will become evident as the description proceeds when taken in connection with the accompanying drawings and examples as best described hereinbelow.

DETAILED DESCRIPTION

I. General Considerations

Figure 1:
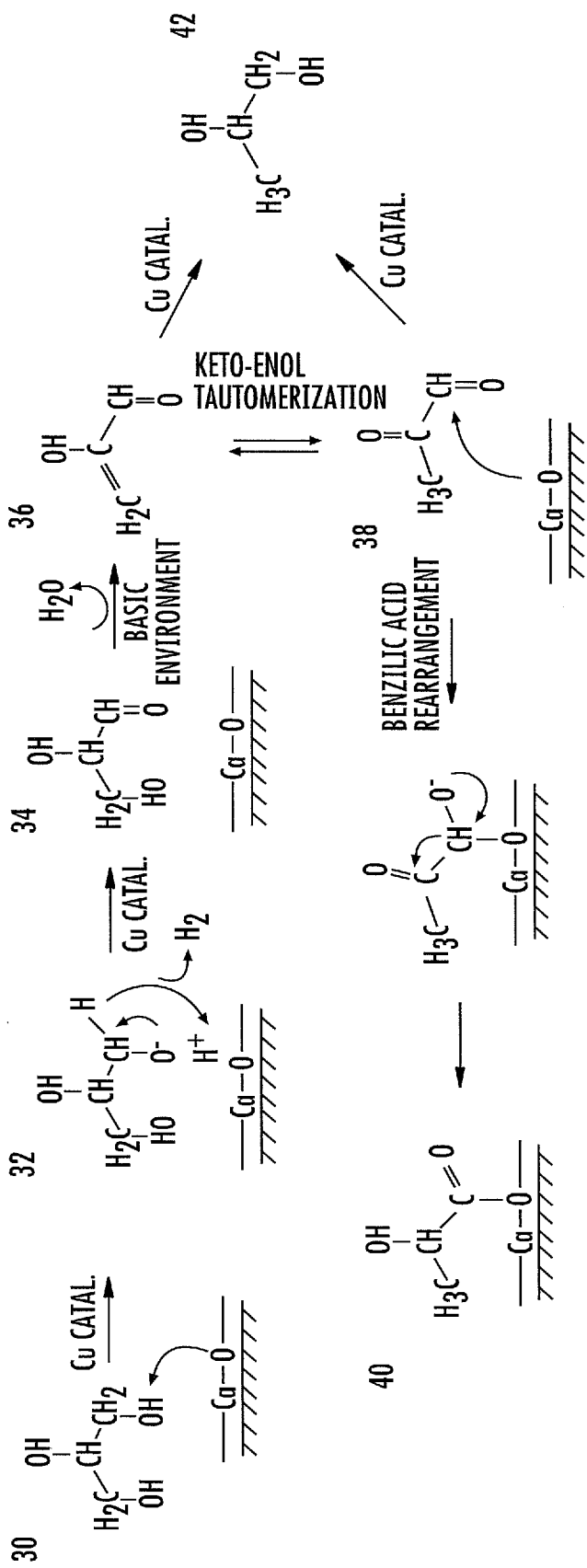
FIG. 1 is a chemical pathway schematic depicting the reaction pathway from glycerol to lactic acid and propylene glycol with CaO and copper-based catalyst.

Development of value-added chemicals and products from glycerol, a co-product of biodiesel production, is necessary to help sustain the biodiesel industry. As such, disclosed herein are methods of converting glycerol to value-added products. In some embodiments, the presently disclosed subject matter provides methods, processes, systems and devices for the simultaneous producing lactic acid and propylene glycol from glycerol. Process modeling and economic analysis of the disclosed methods, processes, systems and devices are also disclosed herein and illustrate the viability of the disclosed technology.

Disclosed herein are methods of simultaneous production of lactic acid (LA) and propylene glycol (PG) from glycerol in a heterogeneous reaction system without external hydrogen supply, wherein glycerol (or maybe water) is in the liquid phase, and a base ingredient and a dehydrogenation catalyst ingredient are in the solid form. In some embodiments, highly concentrated glycerol (best 100%) can be used for maximal productivity because of the relative low corrosiveness of solid based. In some embodiments, the solid base can be but not constrained, to alkaline earth metal oxide (e.g. MgO, CaO, and SrO) and alkaline earth metal (e.g. $Mg(OH)_2$ and $Ca(OH)_2$). In some embodiments, the dehydrogenation metal catalysts can be but are not constrained to Cu, $Cu_2O$, CuO, and copper chromite. In some embodiments, the lactic acid (LA) produced is racemic with a molar ratio of L-(+)-lactic acid to D-(−)-lactic acid around 1. In some embodiments, unlike existing glycerol-to-propylene glycol conversions which require high-pressure external hydrogen supply, the disclosed methods use the hydrogen generated in-situ, simplifying the process and improving the efficiency. $H_2$ production is a necessary step during glycerol-to-lactic acid conversion, whereas $H_2$ is required during glycerol-to-propylene glycol conversion. In some embodiments, the catalysts are reusable after certain regeneration procedures. A portion of base catalyst cannot be recovered, but the dehydrogenation ingredient is fully recoverable. An advantage of using CaO is its easy availability and relative inexpensiveness. The resulted $CaSO_4$ waste may be sold as a construction material, depending on the quality. In some embodiments, by controlling the water percentage, the ratio of different starting materials and pressure, the ratio of lactic acid and propylene can be tuned to a large degree. In some embodiments, crude glycerol from biodiesel production can be directly used in this process to reduce the production cost. In some embodiments, compared with glycerol-to-lactic acid conversion using a homogeneous system, the post-processes to separate catalysts from the products are less expensive for this heterogeneous approach. A complete process from starting materials to marketable LA and PG products are designed and disclosed.

Methods using solid catalysts to simultaneously produce lactic acid (LA) and propylene glycol (PG) are disclosed herein. Compared to the alternative approaches to producing lactic acid from glycerol, the disclosed methods, process and systems achieved higher productivity while substantially reducing corrosion problems. Different combinations of catalysts and reaction conditions provide in some embodiments tunable ranges for the yields of LA and/or PG.

In some embodiments, the combined usage of a base ingredient, e.g. a solid base, and a dehydrogenation ingredient, e.g. a copper-based catalyst, provides a heterogeneous catalytic pathway to convert glycerol to racemic LA. During the glycerol-to-lactic acid conversion, hydrogen can be formed, which can be used in situ to generate PG, another high-value chemical from glycerol. In some embodiments, and as discussed further herein, the effects of temperature, reaction time, catalysts, and water content can impact the efficiency and effectiveness of glycerol conversion to value-added products, e.g. LA and/or PG. By way of example and not limitation, in some embodiments the yields of LA and PG can be optimized in the range of about 50-70 mol % and 17-30 mol %, respectively, with corresponding glycerol conversion of 87-95 mol %, using methods, processes, systems and devices as disclosed herein. In some embodiments, the LA produced is racemic with a molar ratio of L-(+)-lactic acid to D-(−)-lactic acid around 1. Throughout the specification and claims, a given chemical formula or name shall encompass all optical and stereoisomers, as well as racemic mixtures where such isomers and mixtures exist, unless as otherwise specifically indicated.

In some aspects, methods, processes, systems and devices as disclosed herein can convert crude glycerol, as opposed to purified or concentrated glycerol, to LA and/or PG. In some embodiments, crude glycerol can be from biodiesel production can be used. Alternatively, in some embodiments, highly concentrated glycerol, such as for example 70%, 75%, 80%, 85%, 90%, 95% or 100% concentrated glycerol, can be used for the maximal productivity because of the relative low corrosiveness of the solid base (e.g., alkaline earth metals and other Louis bases). In another embodiment, different water percentages in the glycerol stock can be used to tune product composition. In still other embodiments, different starting materials can be used to tune product composition. In other embodiments, different pressures can be used to tune product composition.

In some embodiments, the dehydrogenation ingredient, or dehydrogenation metal catalysts, can be, but are not limited to, Cu, Cu$_2$O, CuO, copper ore or copper chromite. In some embodiments, the base ingredient, or base-modifying solid can be, but is not limited to, an alkaline earth metal oxide (e.g. MgO, CaO, and SrO) and/or an alkaline earth metal. In some embodiments, the dehydrogenation catalyst is recoverable and recyclable in the method of converting glycerol.

II. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, systems, processes, devices, and materials similar or equivalent to those described herein can be used in the practice or testing of the presently disclosed subject matter, representative methods, systems, processes, devices, and materials are now described.

Following long-standing patent law convention, the terms "a" and "an" mean "one or more" when used in this application, including the claims.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, "significance" or "significant" relates to a statistical analysis of the probability that there is a non-random association between two or more entities. To determine whether or not a relationship is "significant" or has "significance", statistical manipulations of the data can be performed to calculate a probability, expressed as a "p value". Those p values that fall below a user-defined cutoff point are regarded as significant. In some embodiments, a p value less than or equal to 0.05, in some embodiments less than 0.01, in some embodiments less than 0.005, and in some embodiments less than 0.001, are regarded as significant. Accordingly, a p value greater than or equal to 0.05 is considered not significant.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a construct or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

III. Methods, Processes and Systems for Converting Glycerol to Lactic Acid and Propylene Glycol Multiple reactions occur during the glycerol conversion process with solid alkaline earth metal oxides, some of which are summarized in Equations 1-5 (see below). Equations 1 and 2 describe the overall equations for glycerol conversion to LA and PG, respectively. During the reaction process, hydrogen generated from LA formation can be used in-situ in the conversion of glycerol to PG. Released in situ, H$_2$ molecules can instantaneously have good contact with the active centers on the copper catalyst and adsorbed glycerol, minimizing the adsorption process to catalyst surface. Meanwhile, CuO (Equation 4) or Cu$_2$O (Equation 5) can be gradually reduced to Cu, which is less catalytically active for dehydrogenation. The reaction rate decreases due to this reduction of copper catalysts (e.g., Cu$_2$O can be reduced to Cu during the reaction course); continuous consumption of CaO and the reactant also accounts for the decrease in the reaction rate of LA and/or PG formation.

$$2C_3H_8O_3 + CaO \rightarrow Ca(C_3H_5O_3)_2 + 2H_2 + H_2O \quad \text{Equation 1}$$

(Ca can be replaced by Sr or Mg, depending on the alkaline earth metal oxide used)

$$C_3H_8O_3 + H_2 \rightarrow C_3H_8O_2 + H_2O \quad \text{Equation 2}$$

$$CaO + H_2O \rightarrow Ca(OH)_2 \quad \text{Equation 3}$$

(Ca can be replaced by Sr or Mg, depending on the alkaline earth metal oxide used)

$$CuO + H_2 \rightarrow Cu + H_2O \quad \text{Equation 4}$$

$$Cu_2O + H_2 \rightarrow 2Cu + H_2O \quad \text{Equation 5}$$

FIG. 1 is a schematic illustrating a reaction pathway for the production of the two major products, LA and PG, from the conversion of glycerol, as occurs in some embodiments of the disclosed methods and processes. In some embodiments, the process can initiate with the conversion of glycerol 30 to glyceraldehyde 34 via glyceroxide ion 32. Each of CaO (base ingredient) and Cu-catalyst (dehydrogenation ingredient) can play a role: CaO advances the formation of glyceroxide ion, while Cu-catalyst promotes the hydrogen abstraction. In a basic condition, glyceraldehyde 34 can be converted to 2-hydroxypropenal 36, which can readily convert to pyruvaldehyde 38 via ketoenol tautomerization (no catalyst is necessary in this step). Hydrogen addition can occur to both 2-hydroxypropenal 36 and pyruvaldehyde 38, and PG 42 can be formed as the result (a catalyst can in some embodiments be employed in this step). Pyruvaldehyde 38 can also undergo benzilic acid rearrangement with the assistance of CaO, and calcium lactate 40 can be formed down this path.

In some embodiments, a method of converting glycerol to LA and/or PG can comprising providing liquid glycerol (or glycerol stock), providing a heterogeneous catalyst, and reacting the liquid glycerol with the heterogeneous catalyst to thereby convert the glycerol to a product mixture comprising LA and/or PG. Notably, in some embodiments, reacting the liquid glycerol with the heterogeneous catalyst can cause simultaneous production of LA and/or PG. As noted above, in some aspects the heterogeneous catalyst can comprise a base ingredient and a dehydrogenation ingredient.

As noted above, a solid base (base ingredient) can in some embodiments play a role in the formation of a glyceroxide ion. For example, benzilic acid rearrangement (formation from pyruvaldehyde to LA) usually occurs in a basic environment. In addition, the base can react with LA via acid-base reaction to form lactate, which not only can shift the reaction equilibrium toward LA formation, but also help protect LA from decomposing or polymerizing. Therefore, a base can in some embodiments play a role in the glycerol-to-LA conversion.

In some embodiments disclosed herein, glycerol-to-LA conversion was studied with the presence of only CaO as a catalyst. An about 40% yield of LA (the only major HPLC-detectable product) with a 97.4% glycerol conversion was detected when 0.4 mol CaO was used per mol glycerol at an optimized reaction condition (290° C. for 150 minutes). An advantage of this protocol is that it is free of solvent. This results in overall higher productivity, and reduced energy consumption, as compared to existing methods, since heating the solvent to the desired temperature is not required. However, over 50% carbon loss was observed, which, without being limited to any one theory, may be due to polymerization (products lost in the solid phase) and/or decomposition ($CO_2$ lost in the gas phase). Without being bound by any particular theory, it is possible that high temperatures favored these undesirable reactions. As such, the presently disclosed subject matter seeks improved methods, systems and compositions comprising in some embodiments an additional catalytic ingredient to further decrease the activation barrier and to allow the formation of LA occurring at a lower temperature.

In some embodiments, in a method of converting glycerol to LA, dehydrogenation of glycerol to glyceraldehyde can be an initial step, where one hydrogen molecule is released from one glycerol molecule. The addition of a dehydrogenation catalyst can in some aspects assist the transition of glycerol to glyceraldehyde, and ultimately catalyze the glycerol-to-LA conversion. Therefore, in some aspects the presently disclosed subject matter is directed to incorporating both a base ingredient and a dehydrogenation ingredient in a catalyst design for converting glycerol to LA.

Copper-containing catalysts can in some aspects catalyze dehydrogenation reactions. Therefore, a comparison among several copper-containing catalysts, including copper (Cu), cuprous oxide ($Cu_2O$), copper oxide (CuO), copper chromite ($Cu_2Cr_2O_5$) and barium promoted copper chromite (Ba—$Cu_2Cr_2O_5$), is disclosed herein.

In some embodiments, any catalysts suitable for hydrogenolysis can be employed in the disclosed methods and systems. The first step of converting glycerol to lactic acid generates hydrogen, so any hydrogenolysis catalyst can in some embodiments generate $H_2$ which can then be used to generate PG.

Experiments were designed and conducted to focus on the base ingredient. Comparisons were conducted among 1) different dosages of CaO (0, 0.1 mol, 0.2 mol, 0.3 mol, 0.4 mol and 0.5 mol per mole of glycerol), and 2) different solid bases, i.e. base ingredients, (MgO, CaO, SrO). CaO was included in the analysis since it is relatively cost effective and readily available, has good basicity, and the preliminary analysis demonstrated positive outcomes.

Thus, in some aspects, the dehydrogenation ingredient used in a method of converting glycerol to LA and/or PG can comprise a metal catalyst, such as for example, copper (Cu), cuprous oxide ($Cu_2O$), copper oxide (CuO), copper chromite ($Cu_2Cr_2O_5$), barium promoted copper chromite (Ba—$Cu_2Cr_2O_5$) and copper ore. In some aspects, the base ingredient used in a method of converting glycerol to LA and/or PG can comprise an alkaline earth metal, such as for example magnesium oxide (MgO), calcium oxide (CaO), and strontium oxide (SrO). In some aspects, the base ingredient used in a method of converting glycerol to LA and/or PG can comprise any solid base with a strong or relatively strong basicity.

In some aspects, in a method of process as disclosed herein the base ingredient and dehydrogenation ingredient of the heterogeneous catalyst can be mixed prior to and/or during the reaction. By way of example and not limitation, a heterogeneous catalyst mixture can comprise CaO and $Cu_2O$. Alternatively, or in addition, in some embodiments, the dehydrogenation ingredient can be supported on the base ingredient. By way of example and not limitation, a base supported dehydrogenation ingredient can comprise $Cu_2O$ supported on CaO. In some embodiments, CuO can be supported on CaO; $Cu_2O$ or CuO can be supported on SrO; and $Cu_2O$/CuO and CaO can be supported on a mesoporous support such as alumina or silica.

In some embodiments, the dehydrogenation ingredient can be recoverable and can be recycled in the method of converting glycerol to lactic acid and propylene glycol. That is, in some embodiments a method or process of converting glycerol as disclosed herein can comprise a step of regenerating spent catalyst. For example, where $Cu_2O$ and CaO are used as the dehydrogenation and base ingredients, respectively, the spent catalysts can be $Ca(OH)_2$ and Cu. The regeneration process can comprise a calcination process wherein the regenerated catalyst comprise CaO and CuO. Such regenerated catalysts can in some embodiments be recycled and used in the conversion of glycerol to LA and/or PG.

The reaction conditions under which one or more of the disclosed methods, processes and systems are performed can vary depending on the desired outcome. In some embodiments, the molar ratio of the dehydrogenation ingredient, e.g. $Cu_2O$, to glycerol can range from about 0.02 to about 0.20. In some embodiments, the molar ratio of the dehydrogenation ingredient to glycerol can range from about 0.04 to about 0.08. In some embodiments, the molar ratio of the dehydrogenation ingredient to glycerol can be about 0.02, about 0.03, about 0.04, about 0.05, about 0.06, about 0.07, about 0.08, about 0.09, about 0.10, about 0.12, about 0.14, about 0.16, about 0.18, or about 0.2.

In some embodiments, the molar ratio of the base ingredient, e.g. CaO, to glycerol can range from about 0.2 to about 1.0 In some embodiments, the molar ratio of the base ingredient to glycerol can be about 0.2, about 0.3, about 0.4, about 0.5, about 0.6, about 0.7, or about 0.8.

In some embodiments, the molar ratio of the dehydrogenation ingredient to the base ingredient can range from about 1:2 to about 1:20. In some embodiments, the molar ratio of the dehydrogenation ingredient to the base ingredient can be about 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or about 1:20.

The effects of reaction temperature and time on glycerol conversion and product selectivity are disclosed herein. Various combinations of base ingredients and dehydrogenation ingredients (for example, CaO and $Cu_2O$) based on results presented herein were used. Desirable conditions for this combination of catalysts were identified. However, in some embodiments it can be challenging to efficiently regenerate the spent catalysts to $Cu_2O$. As such, further attempts were undertaken to explore the combined usage of CaO and CuO (CaO&CuO) and that of CaO and Cu (CaO&Cu), since regenerating CuO can be more effective that regenerating $Cu_2O$. Reactions with such catalyst combinations were conducted at various temperatures and for various lengths of time, with the objective of finding the optimal conditions for this value-added production considering good yields of LA and/or PG and the simplicity of recycling the catalysts.

Based on the above, and as detailed further in the Examples below, in some embodiments, the reaction can occur at about 160° C. to about 270° C. for about 40 minutes to about 180 minutes. In some embodiments, the reaction can occur at about 160° C., about 170° C., about 180° C., about 190° C., about 200° C., about 210° C., about 220° C., about 230° C., about 240° C., about 250° C., about 260° C., or about 270° C. In some embodiments, the reaction can occur for about 40 minutes, about 50 minutes, about 60 minutes, about 70 minutes, about 80 minutes, about 90 minutes, about 100 minutes, about 110 minutes, about 120 minutes, about 130 minutes, about 140 minutes, about 150 minutes, about 160 minutes, about 170 minutes, or about 180 minutes.

In some aspects, one or more of the methods, systems and processes disclosed herein for converting glycerol to LA and/or PG can be tuned or optimized by adjusting or modifying the stock ingredient, e.g. glycerol, and/or one or more of the operating conditions or parameters. By way of example and not limitation, the efficiency of conversion of glycerol and the yield of lactic acid and propylene glycol can be increased or decreased by one or more of the following factors: the concentration of water in the glycerol; the purity of the glycerol; or the pressure under which the reaction occurs. For example, properties and characteristics of the glycerol feedstock can impact the efficiency and production characteristics of a glycerol conversion. In some embodiments, a highly concentrated or purified glycerol stock can be used wherein the highly concentrated or purified glycerol can comprise glycerol with a purity of about 70% to about 100% (70%, 75%, 80%, 85%, 90%, 95% or 100%). In some embodiments, a crude glycerol stock can be used. In some embodiments, crude glycerol can comprise about 75% to about 85% glycerol (75%, 80%, 85%) and about 5% to about 15% water (5%, 10%, 15%), wherein the crude glycerol can also have a pH of about 6 to about 12. In some aspects, the source of glycerol can be from biodiesel production or similar renewable fuel production system. In some embodiments, the glycerol can be from any source. In some aspects, the pressure can range from about 500 psi to about 2,000 psi, or more. In some embodiments, the pressure can be an autogeneous pressure for a sealed system. In some embodiments, increasing the pressure, e.g. above 500 psi, or above 1,000 psi, or above 1,500 psi, or above 2,000 psi can favor, or enhance, PG generation as compared to a lower pressure.

Figure 2:
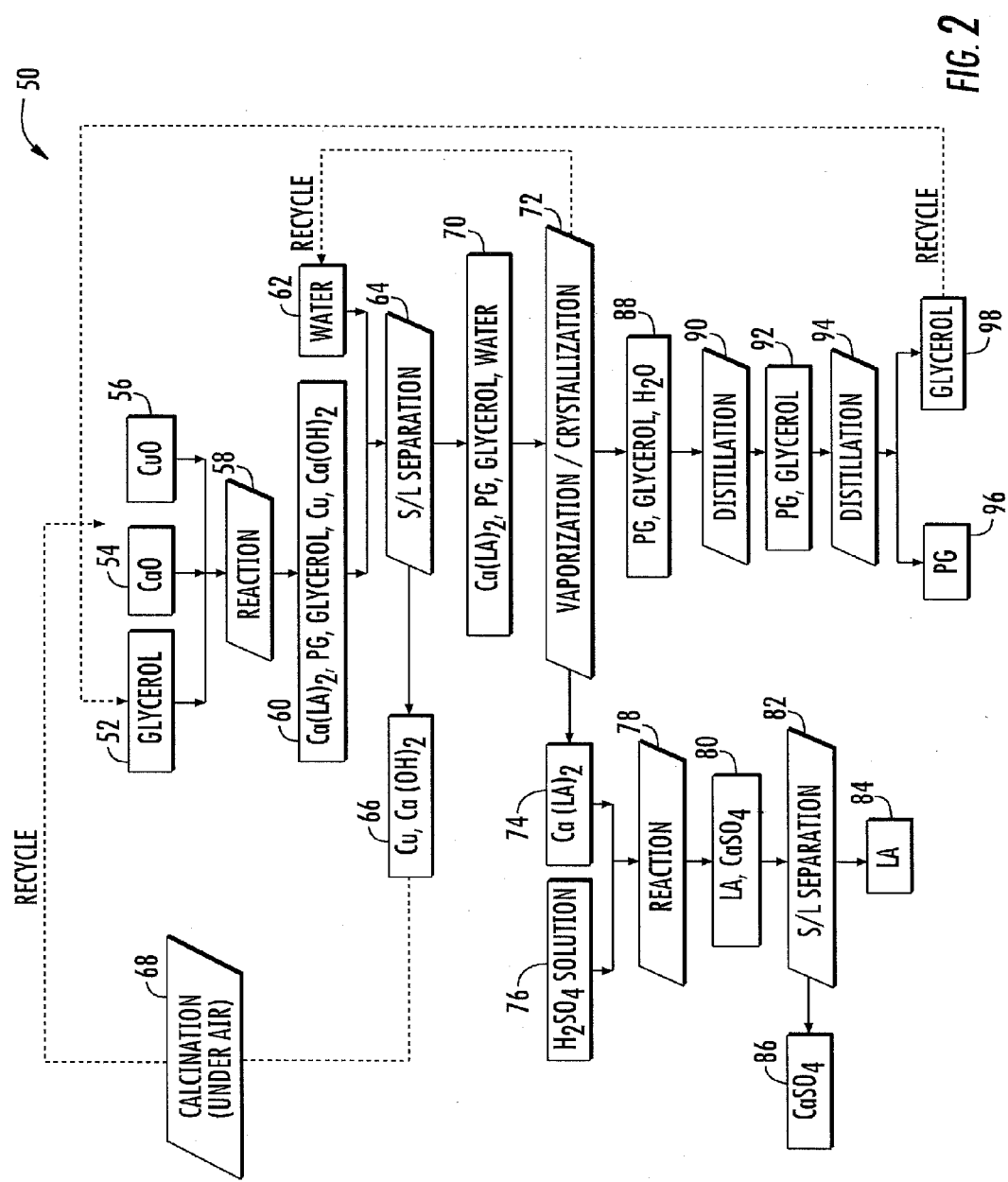
FIG. 2 depicts a flow diagram of a process design for lactic acid and propylene glycol production from glycerol.

Disclosed herein are processes and systems for LA and/or PG production from glycerol based on the disclosed conversion methods. FIG. 2 depicts a flow diagram of an exemplary process for LA and/or PG production from glycerol. In a glycerol conversion process 50, as depicted in FIG. 2, glycerol 52, CaO 54 and CuO 56 can be reacted in reaction 58 under the conditions disclosed herein. The products 60 of reaction 58 can be cooled and washed with water 62, and the filtrate 70, containing $Ca(LA)_2$, glycerol and PG, can be separated 64 from the filter cake 66 (containing Cu and $Ca(OH)_2$). In some embodiments, filter cake 66 (containing Cu and $Ca(OH)_2$) can be calcinated 68, after which CuO and a portion of CaO (the rest of CaO is lost in the form of $CaSO_4$ 86; see below) can be recycled back to the beginning of glycerol conversion 50. In some aspects, the filtrate 70 can be fed into a crystallizer 72 where $Ca(LA)_2$ 74 can be precipitated out. $Ca(LA)_2$ 74 can be treated with sulfuric acid solution 76 to be converted via reaction 78 to free lactic acid and $CaSO_4$ 80. The formed $CaSO_4$ 86 in solid phase can be separated 82 from the aqueous phase in a rotary vacuum filter 82. Lactic acid solution 84 can then be concentrated to 90% concentration as final product in a distillation tower. In some aspects, glycerol, propylene glycol and $H_2O$ 88 can be further treated in a two-phase distillation process (90 and 94). A first separation/distillation tower 90 can remove water and a second tower 94 can separate glycerol 98 and PG 96. In some embodiments, glycerol 98 can be recycled to be run through the conversion process 50 again.

Figure 3:
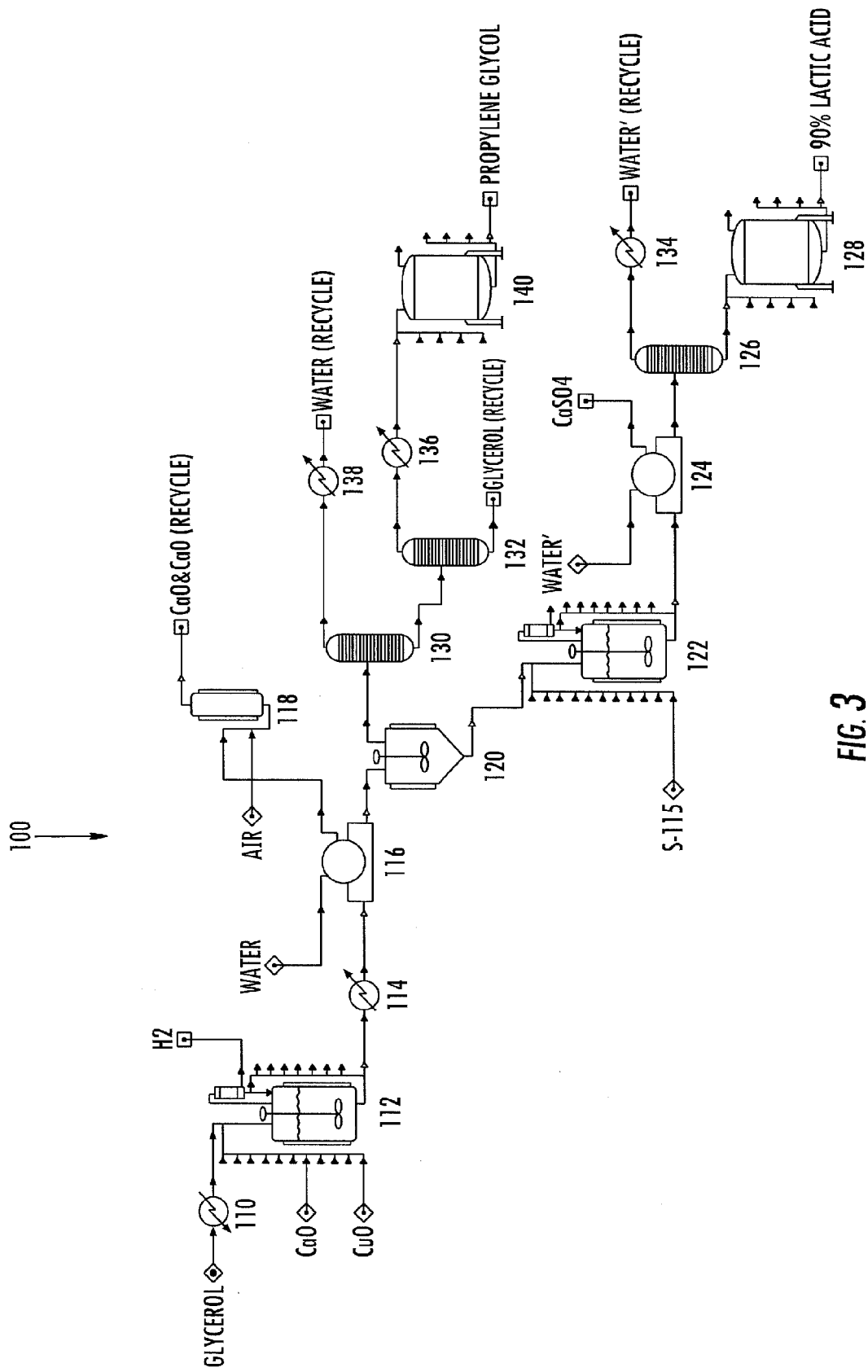
FIG. 3 depicts a system design for lactic acid and propylene glycol production from glycerol.

In some embodiments, a system that converts glycerol to LA and/or PG can comprise a system 100 as depicted in FIG. 3. System 100 can incorporate glycerol conversion, product separation, and regeneration of catalysts. Referring to FIG. 3, glycerol can be preheated in heater 110 to a desired reaction temperature prior to entering reactor 112. In some embodiments, the reaction of glycerol with CaO&CuO can take place in a continuous stirred tank reactor (CSTR) 112. The products can be cooled 114 and washed to a rotary vacuum filter 116, where the filtrate, containing $Ca(LA)_2$, glycerol and PG, can be separated from the filter cake (containing Cu and $Ca(OH)_2$). Filter cake can be delivered in some embodiments to a furnace 118 for calcinations. After calcination, CuO and a portion of CaO (the rest of CaO is lost in the form of $CaSO_4$) can be recycled back to glycerol conversion. The filtrate can be fed into a crystallizer 120, where $Ca(LA)_2$ can be precipitated out. $Ca(LA)_2$ can be treated with sulfuric acid solution in reactor 122 to be converted to free lactic acid and $CaSO_4$. The formed $CaSO_4$ is solid phase and can be separated from the aqueous phase in a rotary vacuum filter 124. In some aspects, lactic acid solution can then be concentrated to 90% concentration as final product in a distillation tower 126. Glycerol and propylene glycol can be separately obtained after two subsequent separation towers, where a first tower 130 removes water and a second tower 132 separates glycerol and PG. The products LA and PG can be stored in containers 128 and 130, respectively, for periodic delivery. In some embodiments, coolers 134, 136 and 138 can provide for liquid condensation.

Figure 4:
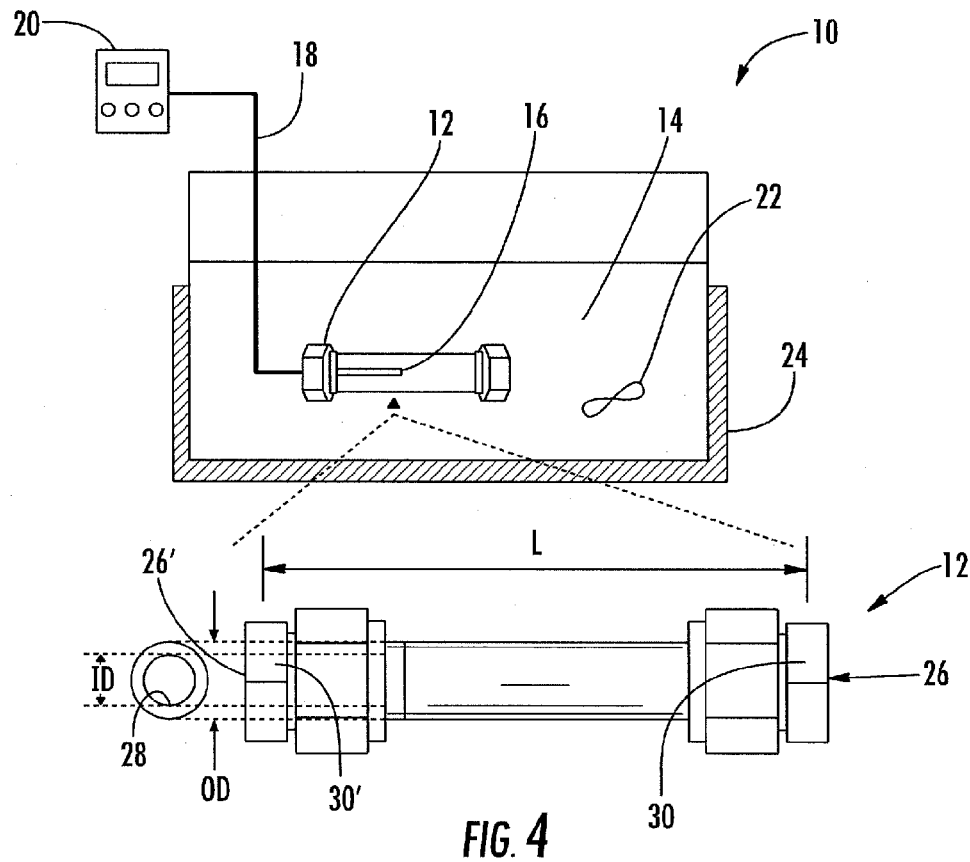
FIG. 4 is a schematic illustration of a reactor for use in the disclosed methods and systems.

In some embodiments, the reaction of glycerol to LA and/or PG can take place in a continuous stirred tank reactor (CSTR), such as that depicted in FIG. 4. A reactor 10 as depicted in FIG. 4 can comprise a reaction vessel 12 submerged in a temperature-controlled oil or salt bath 14 (operation temperature about 150° C. to about 300° C.). In some aspects, reaction vessel 12 can comprise a thermocouple 16, a control device 20 (including for example a temperature control device and/or recorder), and a mechanical or electrical linking member 18 connecting the thermocouple 16 and control device 20. In some aspects, temperature-controlled oil or salt bath 14 can comprise a stirring device 22 and a heating source 24 (e.g. an electronic heating device).

Reaction vessel 12 can comprise a batch reactor made of an enclosed and/or sealed structure, such as for example a cylindrical tube-like structure having a first 26 and second 26' ends and an internal cavity 28. In some aspects, reaction vessel 12 can comprise end caps 30 and 30' for enclosing and/or sealing first 26 and second 26' ends. In some embodiments, reaction vessel 12 can have a length L of about 5 cm to about 15 cm, including for example a length L of about 10.5 cm. In some embodiments, reaction vessel 12 can have an inside diameter ID of about 0.5 cm to about 1.5 cm, including for example an inside diameter ID of about 1.06 cm. In some embodiments, reaction vessel 12 can have an outside diameter OD of about 1.0 cm to about 2.0 cm, including for example an outside diameter OD of about 1.59 cm. In some embodiments, reaction vessel 12 can have internal cavity 28 having a total volume of about 5 mL to about 15 mL, including for example a volume of about 9.27 mL. In some embodiments, reaction vessel 12 can be made of stainless steel (e.g., SS316) or any other suitable metal or other material. In some embodiments, reaction vessel 12 can be loaded with a suitable amount of reactants, depending on the size of the reaction vessel, to be converted to LA and/or PG.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently claimed subject matter.

MATERIALS AND METHODS

General Considerations.

A solid base can in some embodiments play a role in the formation of a glyceroxide ion. For example, benzilic acid rearrangement (formation from pyruvaldehyde to LA) usually occurs in a basic environment. In addition, the base can react with LA via acid-base reaction to form lactate, which not only can shift the reaction equilibrium toward LA formation, but also help protect LA from decomposing or polymerizing. Therefore, a base can in some embodiments play a role in the glycerol-to-LA conversion.

Glycerol-to-LA conversion was studied with the presence of only CaO as a catalyst. An about 40% yield of LA (the only major HPLC-detectable product) with a 97.4% glycerol conversion was detected when 0.4 mol CaO was used per mol glycerol at an optimized reaction condition (290° C. for 150 minutes). An advantage of this protocol is that it is free of solvent. This results in overall higher productivity, and reduced energy consumption since heating the solvent to the desired temperature is not required. However, over 50% carbon loss was observed, which, without being limited to any one theory, may be due to polymerization (products lost in the solid phase) and/or decomposition ($CO_2$ lost in the gas phase). Without being bound by any particular theory, it is possible that high temperatures favored these undesirable reactions. As such, the presently disclosed subject matter seeks improved methods, systems and compositions comprising in some embodiments an additional catalytic ingredient to further decrease the activation barrier and to allow the formation of LA occurring at a lower temperature.

In some embodiments, in a method of converting glycerol to LA, dehydrogenation of glycerol to glyceraldehyde can be an initial step, where one hydrogen molecule is released from one glycerol molecule. The addition of a dehydrogenation catalyst can in some aspects assist the transition of glycerol to glyceraldehyde, and ultimately catalyze the glycerol-to-LA conversion. Therefore, in some aspects the presently disclosed subject matter is directed to incorporating both a base ingredient and a dehydrogenation ingredient in a catalyst design for converting glycerol to LA.

Copper-containing catalysts can in some aspects catalyze dehydrogenation reactions. Therefore, a comparison among several copper-containing catalysts, including copper (Cu), cuprous oxide ($Cu_2O$), copper oxide (CuO), copper chromite ($Cu_2Cr_2O_5$) and barium promoted copper chromite (Ba—$Cu_2Cr_2O_5$), was conducted. While the dehydrogenation ingredient is a variable, the reaction conditions and the base ingredient remained the same, which were 60-minute at 190° C. with CaO in a molar ratio of 0.4 mol/mol to glycerol. To draw a fair comparison, the ratio of dehydrogenation catalyst to glycerol was calculated based on the elemental Cu. A molar ratio of 0.04 moles per mole of glycerol was adopted for the dosage of $Cu_2O$ in some of the disclosed experiments. Therefore, the ratio of 0.04 moles per mole of glycerol was also used for $Cu_2Cr_2O_5$ and barium promoted $Cu_2Cr_2O_5$, but the ratio of 0.08 moles per mole of glycerol was used for Cu and CuO.

Experiments were designed to focus on the base ingredient. Comparisons were conducted among 1) different dosages of CaO (0, 0.1 mol, 0.2 mol, 0.3 mol, 0.4 mol and 0.5 mol per mole of glycerol), and 2) different solid bases (MgO, CaO, SrO). CaO was included in the analysis since it is relatively cost effective and readily available, has good basicity, and the preliminary analysis demonstrated positive outcomes. While the base ingredient was the variable in this particular analysis, the reaction conditions and the dehydrogenation ingredient remained the same, which were 60-minutes at 190° C. with $Cu_2O$ in a molar ratio of 0.04 mol/mol to glycerol.

The effects of reaction temperature and time on glycerol conversion and product selectivity were also assessed. Various combinations of base ingredients and dehydrogenation ingredients (namely, CaO and $Cu_2O$) based on results presented herein were used. Desirable conditions for this combination of catalysts were identified. However, in some embodiments it can be challenging to efficiently regenerate the spent catalysts to $Cu_2O$. As such, further attempts were undertaken to explore the combined usage of CaO and CuO (CaO&CuO) and that of CaO and Cu (CaO&Cu), since regenerating CuO can be more effective that regenerating $Cu_2O$. Reactions with such catalyst combinations were conducted at various temperatures and for various lengths of time, with the objective of finding the desirable conditions for this value-added production considering good yields of LA and/or PG and the simplicity of recycling the catalysts.

Experiments were also conducted to assess the effects of catalysts on the catalytic performance, and particularly the use of mixing two ingredients. CaO supported $Cu_2O$ (denoted as $Cu_2O$-on-CaO) was used for the case study. $Cu_2O$-on-CaO was fabricated via the following procedures. CaO was impregnated with 1 mol/L $Cu(NO_3)_2$ solution for 24 hours, wherein the quantities of CaO and $Cu(NO_3)_2$ were configured stoichiometrically depending on the target ratio of CaO and $Cu_2O$. NaOH solution (1 mol/L) was then added in with stirring, where the total volume of this NaOH solution was determined via calculation to ensure 2 mol NaOH per mole of $Cu(NO_3)_2$. The mixture was aged in air at room temperature for 10 minutes. Then various amount of 1 mol/L $N_2H_4$ solution, prepared from 100% $N_2H_4$, was added in a drop-wise manner to the mixture, and vigorous stirring was applied during the course. The mixture was continuously stirred for another 2 hours before filtration. The filter cake was rinsed with deionized water and dried in a vacuum oven at 60° C. for 3 hours. The solid was then calcinized at 900° C. in a nitrogen atmosphere. The fabricated catalysts were tested at 190° C. for 60 minutes or 75 minutes. The results were compared to the direct usage of CaO and $Cu_2O$ mixture (CaO&$Cu_2O$).

Powder X-ray diffraction (XRD) pattern was used as the assistance to ensure the successful fabrication of $Cu_2O$-on-CaO and to evaluate the spent and regenerated catalysts. XRD spectra were acquired on a Bruker AXS D8 Advance X-ray diffractometer (Bruker Corporation, Billerica, Mass., United States of America) using Cu-Kα radiation (0.15418 nm). The tube voltage and current was 40 kV and 40 mA, respectively. The scanning step size was 0.04° with the rate of 1 s per step. The spectrum was collected for the 2θ range of 2°-80°.

Crude glycerol collected from biodiesel producers were tested under several good reaction conditions that were identified using refined glycerol. Crude glycerol samples were characterized by the following parameters: pH, water content, and glycerol content. Crude glycerol samples were diluted with neutral buffer (pH=7) prior to pH measurements with a pH meter (Extech Instruments, Optimum Energy Products Ltd., Calgary, Alberta, Canada). The pH readings were then back calculated with the known concentration (glycerol in buffer) to obtain the pH of crude glycerol samples. Water content was measured via a Karl Fischer titrator (Schott Instruments, GmbH, Mainz, Germany). Glycerol contents in crude glycerol sample were measured via HPLC. Prior to HPLC, the sample underwent the pretreatment steps of dilution (with DI water), centrifugation and deionization.

To study the economic viability of this technology for glycerol conversion, a production plant turning the starting material of glycerol into the final marketable products was designed. SuperPro Designer (version 8.5, 2011; Intelligen, Inc., Scotch Plains, N.J., United States of America) process simulation software was employed in the development of process models for a 10,000 MT and a 100,000 MT annual production scale of LA. The former capacity is selected considering a common capability of medium-size biodiesel producers. The latter capacity is determined according to the current lactic acid production facility [5]. The specification and production data of the reactors were based on laboratory results. Economic assessment was also performed, providing valuable information to explore the industrial potential of the developed technology.

Materials, Apparatuses and Detailed Procedures.

Cu, CuO, $Cu_2O$ and copper chromite were purchased from Acros Organics (Geel, Belgium). CaO, MgO, and SrO and glycerol (99.7%) were purchased from Fisher Scientific (Thermo Fisher Scientific, Inc., Waltham Mass., United States of America). The catalysts were used as received unless it otherwise specified in the text. Only deionized water was used in all the experiment steps. Crude glycerol sample was supplied by a biodiesel manufacturer. HPLC Chemical standards L-lactic acid (~98%) and D, L-lactic acid (~90%) were purchased from Sigma Aldrich (Sigma-Aldrich Corp., St. Louis, Mo., United States of America). Another HPLC Chemical standard propylene glycol (USP/FCC) was purchased from Fisher Scientific. Sulfuric acid ($H_2SO_4$) used in the treatment of product samples for HPLC analysis was purchased from Fisher Scientific. The reagents used in fabricating $Cu_2O$-on-CaO ($Cu(NO_3)_2$, $N_2H_4$ and NaOH) were purchased from Acros Organics.

Example 1

Glycerol Reaction to Lactic Acid and Propylene Glycol

The reactions were performed in batch reactors made of stainless steel (SS316; 10.5 cm length, 1.06 cm inner diameter (i.d.), 1.59 cm outer diameter (o.d.), and 9.27 mL total volume), the schematic of which was shown in FIG. 4. All parts used for assembling the reactors were purchased from Hy-Lok USA (Hy-Lok USA, Inc., Houston, Tex., United States of America). The reaction temperature regulation was achieved via immersing the sealed reactor in a temperature-controlled oil or salt bath (operation temperature 150° C.-300° C.). Laboratory tests showed that the reactants inside the reactor could achieve desired temperature within 2 minutes. The reactor was filled with approximately 5 g of the reactants (ingredients are to be specified in the experiment design), and completely immersed in the oil/salt bath of desired temperature. After the reaction, the reactor was quenched immediately in an ice-water bath.

The product after reaction was washed out with deionized water (DI water). For analytical purposes, the pH of the diluted product sample was adjusted to around 3 with diluted $H_2SO_4$. All lactate was converted back to lactic acid while the sulfate salt precipitated in the solid form. The resulting mix was well stirred before the samples were withdrawn into 2-mL centrifuge tubes. The samples were centrifuged at $10^4$ rpm for 5 minutes. The clear liquid collected from the upper layer was then fed through an ion-exchange column packed with DOWEX 50WX8-400 resin (Sigma Aldrich) to remove the dissolved metal ions. The deionized sample was analyzed on a HPLC system equipped with a refractive index detector (Waters 410; Millipore Corporation, Milford, Mass., United States of America) and SHODEX™ SH1011 column (Showa Denko America, Inc., New York, N.Y., United States of America). This column did not separate chiral LAs, and therefore quantified LA is the total amount of LA regardless of its chiral property. Diluted sulfuric acid (0.05 g/L) was used as the mobile phase for the HPLC. Lactic acid, glycerol and propylene glycol were well separated, and the quantification of these chemicals in all the samples was conducted using this protocol. For analyzing the chiral distribution of L- and D-LA in the product, which was only performed for each of the different combinations of catalysts, CHIRALPAK® MA(+) column (Chiral Technologies, Inc., West Chester, Pa., United States of America) with the mobile phase of a 0.5 mM $CuSO_4$ solution was used.

Example 2

Definition of Kinetic Parameters

Glycerol conversion was calculated via Equation 6:

$$X_{glycerol} = \frac{n_{reacted}}{n_{feed}} \times 100\% = \frac{n_{feed} - n_{quantified}}{n_{feed}} \times 100\% \quad \text{Equation 6}$$

where $X_{glycerol}$ is glycerol conversion (mol %), $n_{reacted}$ is the moles of glycerol reacted, $n_{feed}$ is the moles of glycerol prior to the reaction, and $n_{quantified}$ is the remaining glycerol in the collected sample quantified by HPLC.

Product (lactic acid or propylene glycol) yield was calculated via Equation 7:

$$Y_{product} = \frac{n_{product}}{n_{feed}} \times 100\% \qquad \text{Equation 7}$$

where $Y_{product}$ is the yield of a specific product formed (LA or PG, mol %), $n_{product}$ is the moles of the specific product (LA or PG), and $n_{feed}$ is the moles of the starting material glycerol.

The selectivity to a specific product (LA or PG) was calculated via Equation 8:

$$S_{product} = \frac{n_{product}}{n_{reacted}} \times 100\% \qquad \text{Equation 8}$$

where $S_{product}$ is the selectivity to lactic acid or propylene glycol (mol %), $n_{product}$ is the moles of either lactic acid or propylene glycol after reaction, and $n_{reacted}$ is the moles of glycerol reacted.

The carbon balance was defined as the total carbon detected in the liquid products (only lactic acid and propylene glycol were included in this study) and in the unreacted glycerol divided by the total carbon in the glycerol feed before the reaction, as calculated via Equation 9:

$$C\% = \frac{\Sigma(C_{quantified-glycerol} + C_{LA} + C_{PG})}{C_{feed}} \times 100\% \qquad \text{Equation 9}$$

where C % is carbon balance (mol %), $C_{quantified-glycerol}$ is carbon content in the remaining glycerol in the collected sample, $C_{LA}$ and $C_{PG}$ are the carbon content in the lactic acid and propylene glycol quantified after the reaction, respectively, and $C_{feed}$ is carbon content in the glycerol feed before the reaction.

Though in some instances it might be desirable to compare these results with previously published studies, different processes can have different concentrations of starting materials, which makes the comparison difficult if only using conversion and yield. Therefore, usually another parameter, the productivity of the desired product, is used to make the evaluation across different processes. The productivity of lactic acid (g min$^{-1}$ L$^{-1}$) is obtained via Equation 10:

$$P_{LA} = \frac{m_{LA}}{t \cdot V} \qquad \text{Equation 10}$$

Where $P_{LA}$ is the volumetric productivity of lactic acid (g min$^{-1}$ L$^{-1}$), $m_{LA}$ is the mass of lactic acid formed during the reaction (g), t is the reaction time (min), and V is the total volume (L) of reactor.

Example 3

Results of Glycerol Reaction

Figure 5:
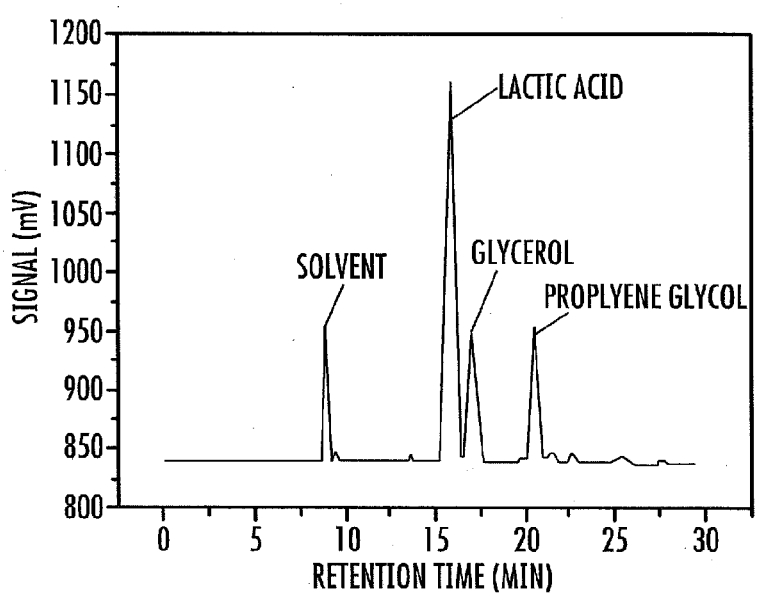
FIG. 5 is a HPLC chromatogram of the product mixture after the reaction of glycerol with a heterogeneous catalyst in a disclosed method of converting glycerol to lactic acid and propylene glycol.

A typical HPLC chromatogram of the product mixture after the reaction (190° C., 60 minutes, refined glycerol (100 wt %), 0.4 CaO/glycerol molar ratio, 0.04 Cu$_2$O/glycerol molar ratio) is shown in FIG. 5. The typical product mixture after the reaction was primarily composed of LA, PG, and unreacted glycerol, which were marked out in the chromatograph. The solvent peak was due to the pH difference between the sample and the mobile phase.

At the end of the reactions, lactic acid existed in the form of calcium lactate, which would be converted to free lactic acid form. The acid form (LA) is used for expressing the results.

Example 4

Effect of Dehydrogenation Catalytic Ingredient

The results of the 60-minute conversion of refined glycerol (conc. 100%) at 190° C. with different copper-containing catalysts are presented in Table 1. Among these investigated copper-containing catalysts, Cu$_2$O showed significantly better performance than the others. Being at its lower oxidation state, Cu$_2$O is very active for the dehydrogenation step. Compared to the usage of CaO alone (38.3% LA yield, 97.4% glycerol conversion, 40.9% carbon balance at a desirable temperature of 290° C. [77]), the combined usage of CaO with Cu$_2$O successfully improved the carbon balance without sacrificing LA yield. Furthermore, PG formation was observed with the presence of the copper-containing catalysts, while it was not a product when CaO was used alone. The reaction occurred at 190° C. (100° C. lower than using CaO alone), which agreed with the hypothesis that undesired polymerization and decomposition reactions were favored at higher temperature.

TABLE 1

Comparison of glycerol conversion, LA yield and PG yield, and carbon balance among different copper-based catalysts. The reactions were conducted at 190° C. for 60 minutes, with 0.4 mol/mol CaO:glycerol in 100 wt % refined glycerol.

| | Cu catalyst | Molar ratio to glycerol | Glycerol conversion % | LA yield % | PG yield % | Carbon balance % |
|---|---|---|---|---|---|---|
| 1 | Cu$_2$O[a] | 0.04 | 79.55 ± 2.07 | 48.24 ± 4.35 | 21.09 ± 2.08 | 89.78 ± 8.27 |
| 2 | CuO[a] | 0.08 | 23.78 ± 1.85 | 11.11 ± 0.38 | 4.77 ± 0.15 | 92.10 ± 2.36 |
| 3 | Cu[a] | 0.08 | 17.45 ± 2.35 | 8.14 ± 1.26 | 1.57 ± 0.44 | 92.26 ± 3.53 |
| 4 | Cu$_2$Cr$_2$O [c] | 0.04 | 11.99 ± 0.50 | 9.92 ± 0.46 | U.D.[b] | 97.96 ± 0.04 |
| 5 | Ba—Cu$_2$Cr$_2$O$_5$[a] | 0.04 | 68.58 ± 1.32 | 40.38 ± 0.45 | 17.62 ± 1.38 | 89.42 ± 2.84 |

[a]Means and standard errors were calculated based on two independent kinetic runs with two repetitive sampling for each run.
[b]Under detection limit.
[c]Means and standard errors were calculated based on one kinetic run with two repetitive sampling for each run.

Example 5

Effect of Base Catalytic Ingredient

Figure 6:
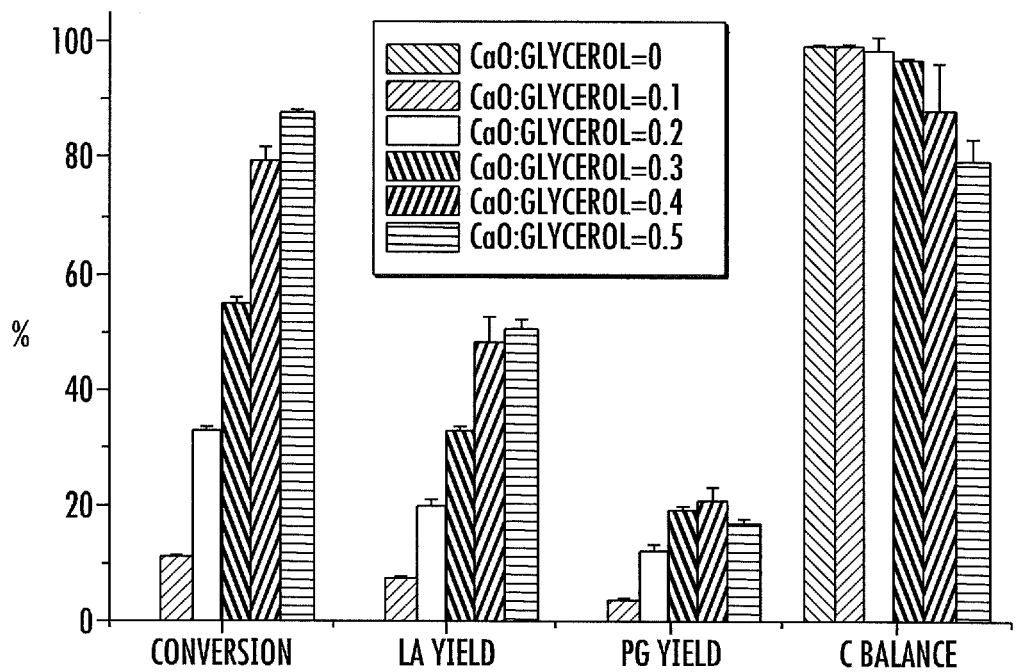
FIG. 6 is a histogram illustrating the results of the conversion of refined glycerol using different dosage of CaO with all the other parameters remaining the same.

The results of the conversion of refined glycerol (conc. 100%) at 190° C. using different dosage of CaO with all the other parameters remaining the same are presented in FIG. 6 (note: standard errors were obtained from two independent kinetic runs with two repetitive samplings for each run). A gradual increase in glycerol conversion was observed with the increase of CaO-to-glycerol molar ratio. There was no glycerol conversion in the absence of CaO at 190° C. When CaO molar ratio increased from 0.1 to 0.4, a clear increasing trend was observed for glycerol conversion and LA yield. The PG yield was significantly increased when CaO molar ratio increased from 0.1 to 0.3. However, further increasing CaO-to-glycerol molar ratio to 0.5 mol/mol did not yield significantly higher LA than that at 0.4 mol/mol ratio. A decrease in carbon balance was observed. Without being bound by any particular theory, it is possible that more decomposition of LA and/or intermediate pyruvaldehyde and/or glyceraldehydes occurred with the presence of higher amount of CaO. In addition, higher dosage of CaO increased the viscosity of reactant mix. Therefore, from a practical point of view, a higher ratio is not necessarily desired. Taking all these factors into account, 0.4 mol/mol CaO-to-glycerol ratio is, in some embodiments, considered a desirable molar ratio for CaO dosage.

Figure 7:
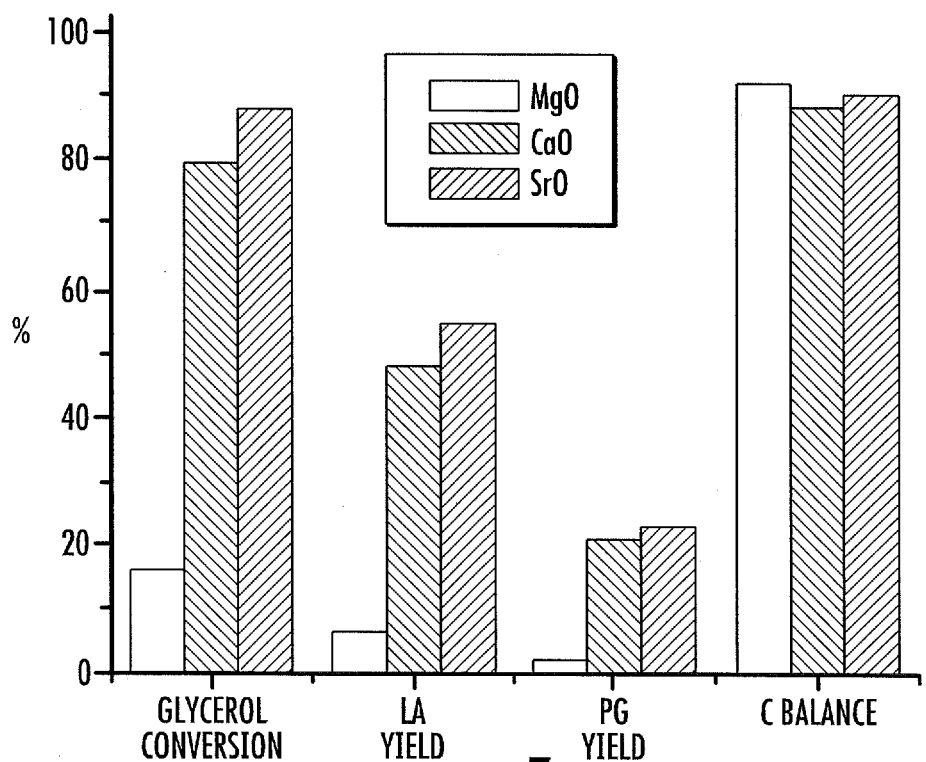
FIG. 7 is a histogram illustrating the results of the conversion of refined glycerol using different solid bases (MgO, CaO, SrO) at the same base-to-glycerol molar ratio.
Figure 8A:
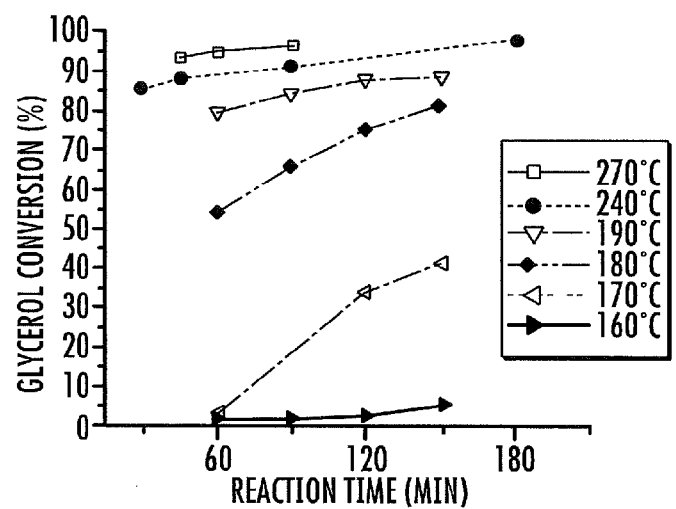
FIGS. 8A-8D are graphical depictions of the effects of temperature and time on glycerol conversion (FIG. 8A), lactic acid selectivity (FIG. 8B), propylene glycol selectivity (FIG. 8C), and carbon balance (FIG. 8D)
Figure 8B:
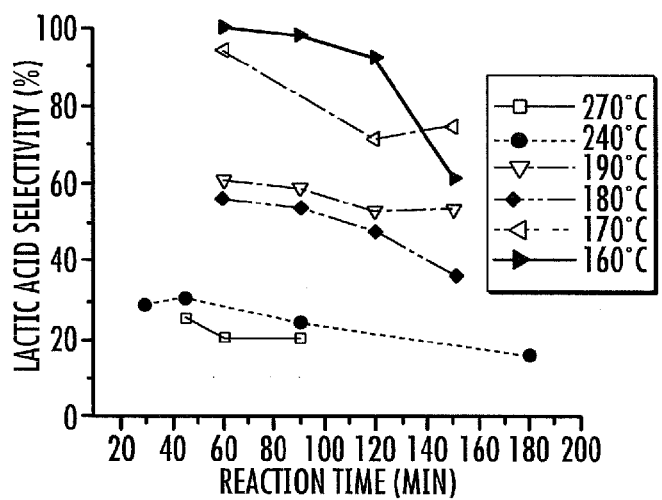
Figure 8C:
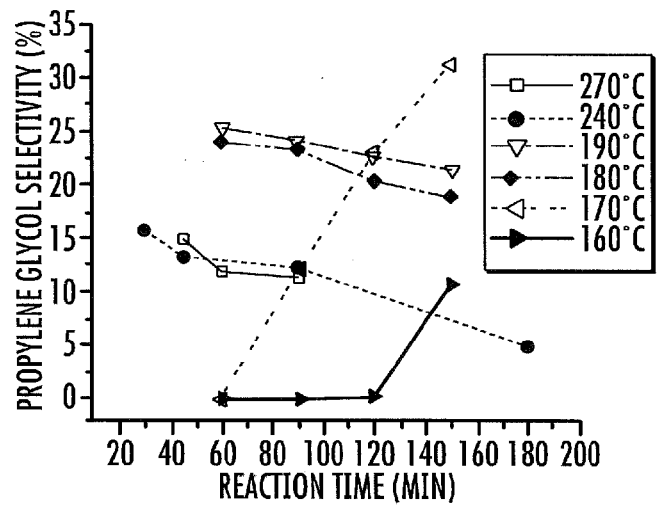
Figure 8D:
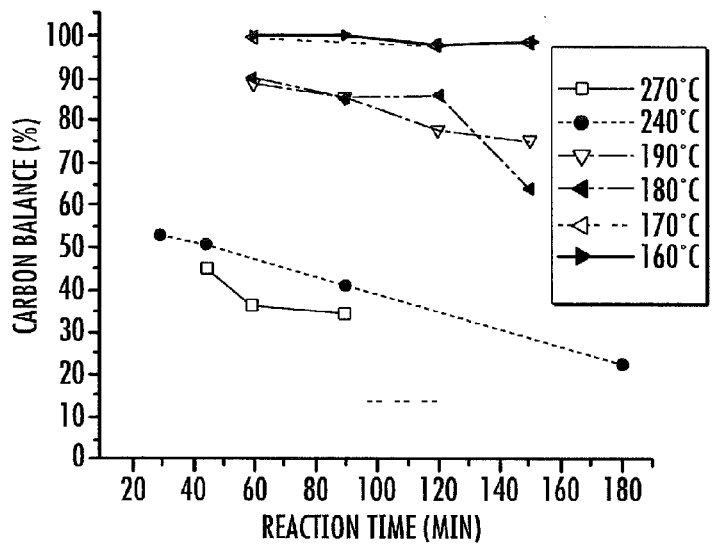

The results of the conversion of refined glycerol (conc. 100%) using different solid bases (MgO, CaO, SrO) at the same base-to-glycerol molar ratio are presented in FIG. 7; all the reactions were conducted at 190° C. for 60 minutes with $Cu_2O$ (0.04 mol/mol glycerol) in addition to the solid base. The catalytic activities were in the order of SrO>CaO>MgO, which coincided with the base strength of these solid bases (MgO 6.8-8.2; CaO 13.4-15.0; SrO 15-17.2). Comparing to glycerol conversion of 79.6% with CaO at 190° C., glycerol conversion achieved with SrO was 87.5%, while there was very small amount of glycerol converted at 190° C. when MgO was used. Although SrO leads to higher conversion and yields compared to CaO, SrO ($2000-3000/MT) is much more expansive than CaO ($100-250/MT) (Price inquiry from international trading site Alibaba.com). Such an improvement in conversion and yields does not necessarily justify the usage of SrO over CaO; therefore, CaO remained a better choice for the base ingredient.

Example 6

Effect of Temperature and Reaction Time

The effects of temperature and time were studied using CaO (0.4 mol/mol glycerol) and $Cu_2O$ (0.04 mol/mol glycerol), the results of which are depicted in FIG. 8. Glycerol conversion (FIG. 8A) increased as the reaction temperature increased or as the reaction time extended. The selectivity to PG (FIG. 8C) and LA (FIG. 8B) displayed a decreasing trend with the increase of reaction time. Temperature higher than 190° C. was generally unfavorable to LA selectivity. For the reaction occurred at and above 180° C., PG selectivity decreased with the increase of temperature and reaction time, which was consistent with the trend of the selectivity to LA. Decrease in the selectivities to LA and PG accounted for the decrease in carbon balance (FIG. 8D) as the reaction temperature and time increased, since only LA, PG and remaining glycerol were considered in the carbon balance calculation. Without being bound by any particular theory, the possible cause for the poorer carbon balance at higher temperature may be due to the decomposition of pyruvaldehyde and lactic acid, which adversely influenced the production of LA and/or PG. However, when reaction temperature was below 180° C. and glycerol conversion was low, an increasing trend with reaction time in PG selectivity was observed. Highest LA yield achieved with this catalyst combination was 48.24%, which occurred at 190° C. with 60 minutes reaction time; corresponding PG yield and glycerol conversion were 21.09% and 79.55%, respectively.

Example 7

Solid Base Support Copper Catalyst

Figure 9:
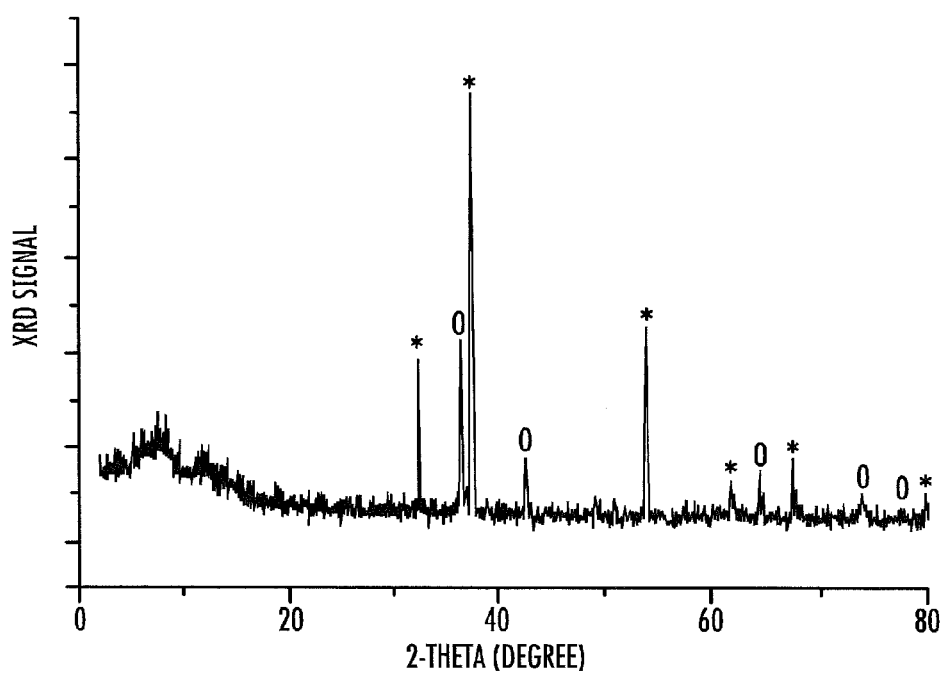
FIG. 9 is a chromatogram of the results of X-ray diffraction analysis of CaO supported $Cu_2O$ heterogeneous catalyst.

Experiments were conducted to prove the concept that CaO supported $Cu_2O$ ($Cu_2O$-on-CaO) would improve the catalytic performance than direct usage as a mixture (CaO&$Cu_2O$). The $Cu_2O$-on-CaO catalyst was prepared by chemical reduction combined with impregnation using CaO as the support and hydrazine hydrate as the reducing agent. X-ray diffraction (XRD) evaluation (FIG. 9) confirmed that all Cu existed in +1 active valence state in the oxide as desired. In FIG. 9 the peaks marked with "*" are the characteristic peaks of CaO, whereas the peaks marked with "o" are characteristic peaks of $Cu_2O$.

Higher glycerol conversion and higher PG yield were observed with $Cu_2O$-on-CaO, compared to simple physical mixture of CaO and $Cu_2O$ (CaO&$Cu_2O$), as presented in Table 2. For illustration purposes only, two data sets are highlighted in Table 2 where the active ingredients had the same molar ratios to glycerol for both CaO-on-$Cu_2O$ and CaO&$Cu_2O$. The results of the highlighted data sets show that Glycerol conversion, LA yield and PG yield were 89.8%, 48.8% and 28.1% with $Cu_2O$-on-CaO after a 60-minute reaction at 190° C., while conversion, LA yield and PG yield were 79.6%, 48.2% and 20.1% using CaO&$Cu_2O$.

The molar ratio of PG to LA in the product increased with the increase percentage of $Cu_2O$. For example, for 60-minute reactions, the PG-to-LA ratio was 0.66, 0.60, 0.58 and 0.39 for $Cu_2O$-on-CaO with the $Cu_2O$ to CaO ratio of 1:3, 1:5, 1:10 and 1:20, respectively. Such a trend was also observed for CaO&$Cu_2O$. Several conditions provided good kinetic results; >50% LA yield and >30% PG yield with >90% glycerol conversion were achieved. Although the supported catalyst provided better performance, the disadvantage is that the fabrication process is time-consuming and more expensive compared to directly using CaO and $Cu_2O$ mixture. The result served as a conceptual proof and provided a choice for approaches.

TABLE 2

Glycerol conversion, yields of lactic acid (LA) and propylene glycol (PG), and carbon balance for different catalysts and reaction conditions. The reaction temperature was 190° C.

| $Cu_2O:CaO$ (molar ratio) | CaO:gly (molar ratio) | $Cu_2O$:gly (molar ratio) | Time (min) | Glycerol Conversion (%) | LA Yield (%) | PG Yield (%) | Carbon Closure (%) | PG:LA (molar ratio) |
|---|---|---|---|---|---|---|---|---|
| CaO supported $Cu_2O$ ($Cu_2O$-on-CaO) | | | | | | | | |
| 1:3 | 0.271 | 0.090 | 60 | 83.2[a] | 43.1 | 28.5 | 88.4 | 0.66 |
| 1:5 | 0.332 | 0.066 | 60 | 91.7 | 52.4 | 31.4 | 89.4 | 0.60 |
| 1:5 | 0.332 | 0.066 | 75 | 93.3 | 50.0 | 30.7 | 86.8 | 0.61 |
| 1:10 | 0.400 | 0.040 | 60 | 89.9 | 48.8 | 28.1 | 86.1 | 0.58 |
| 1:10 | 0.400 | 0.040 | 75 | 93.3 | 52.5 | 29.0 | 87.4 | 0.55 |
| 1:20 | 0.445 | 0.022 | 60 | 80.3 | 41.0 | 16.1 | 75.3 | 0.39 |
| 1:20 | 0.445 | 0.022 | 75 | 88.4 | 37.6 | 15.9 | 63.9 | 0.42 |
| Physical mixture (CaO&$Cu_2O$) | | | | | | | | |
| 1:3 | 0.271 | 0.090 | 60 | 71.8 | 39.7 | 26.8 | 93.5 | 0.68 |
| 1:3 | 0.271 | 0.090 | 90 | 72.2 | 38.2 | 26.5 | 91.2 | 0.69 |
| 1:3 | 0.271 | 0.090 | 150 | 74.1 | 38.8 | 28.0 | 91.7 | 0.72 |
| 1:5.8 | 0.349 | 0.060 | 150 | 82.3 | 49.0 | 28.5 | 94.0 | 0.58 |
| 1:10 | 0.400 | 0.040 | 60 | 79.6 | 48.2 | 20.1 | 88.7 | 0.42 |

[a]All the data are the average of two independent runs with repetitive samplings for each run.

Example 8

Systematic Comparison Among $Cu_2O$, CuO, and Cu

Figure 10:
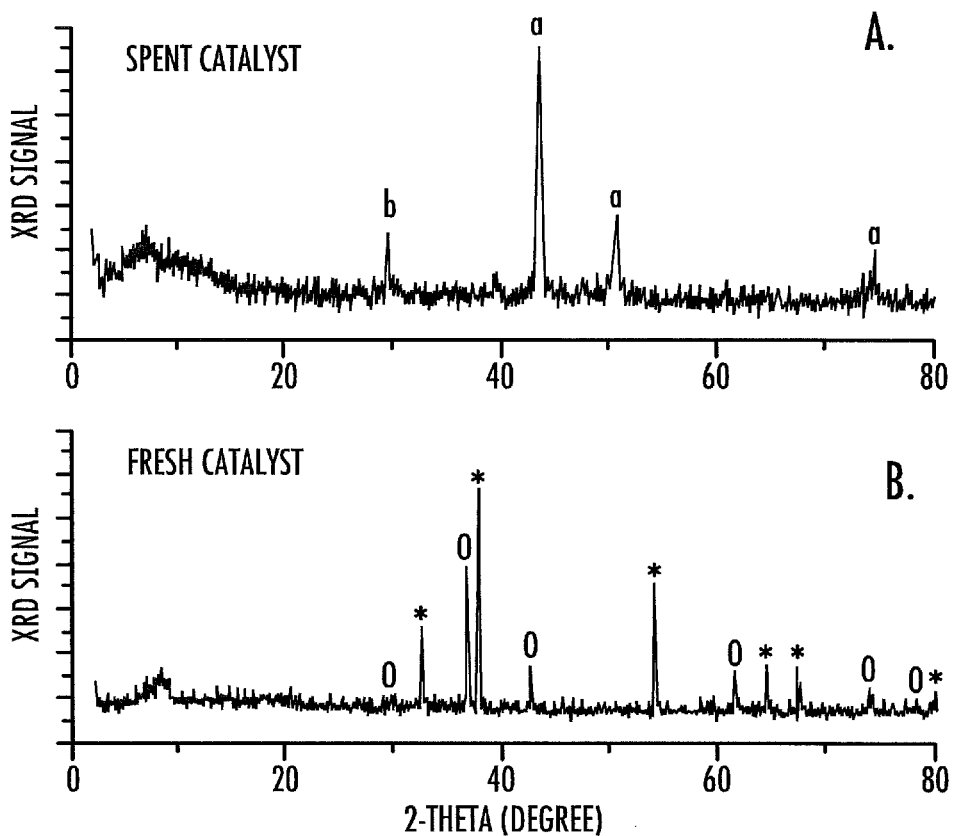
FIGS. 10A and 10B are X-ray diffraction patterns showing the results of X-ray diffraction analysis of spent $Cu_2O$&CaO (FIG. 10A) versus fresh $Cu_2O$&CaO (FIG. 10B) catalysts.

In exploring the potential to reuse spent catalysts (CaO&$Cu_2O$, CaO&CuO, and CaO&Cu), it was discovered that most $Cu_2O$ was reduced to Cu during the reaction. This is evidenced in FIG. 10, the XRD figure of the spent catalyst (FIG. 10A) obtained after filtration. The peaks marked with "a" matched the characteristic peaks of copper metal, evidencing the existence of copper. Without being bound by any particular theory or mechanism of action, it is possible that the occurrence of such a reduction of $Cu_2O$ may be due to its exposure to in-situ generated $H_2$ elevated temperatures. No peak that associated with original calcium compounds was observed on the XRD, suggesting either that there were no calcium compound(s) in the spent solid catalysts or that they existed in an amorphous form. The position of the peak marked as "b" is one of the characteristic peaks of $Cu_2O$, while most of the characteristic peaks of $Cu_2O$ were not observed. The possible explanation was that during the reaction, most crystal surfaces of $Cu_2O$ were destroyed. In FIG. 10B the peaks marked with "*" are the characteristic peaks of CaO, whereas the peaks marked with "o" are characteristic peaks of $Cu_2O$.

CaO reacts with LA to form $Ca(LA)_2$ ($2C_3H_6O_3$+CaO→$Ca(C_3H_5O_3)_2$+$H_2O$). Stoichiometrically, the rest of CaO would be converted to $Ca(OH)_2$ due to the reaction with $H_2O$. Calcium carbonate ($CaCO_3$) could also form since some $CO_2$ can be present in the system, possibly from some of the decomposition reactions or from the air (when the product mix was exposed to air during post-treatment). Most of $Ca(OH)_2$ (and/or $CaCO_3$) was in the solid phase after washing out the product mix with water. $Ca(OH)_2$ (and/or $CaCO_3$) can be easily regenerated to CaO via calcination at 910° C. $Ca(OH)_2$ started to decompose into CaO at 512° C. During the process, $CO_2$ and $H_2O$ continued to evolve from $Ca(OH)_2$ and $CaCO_3$; the deposited polymerization products would undergo combustion in air, also resulting in $CO_2$ and $H_2O$.

Figure 11:
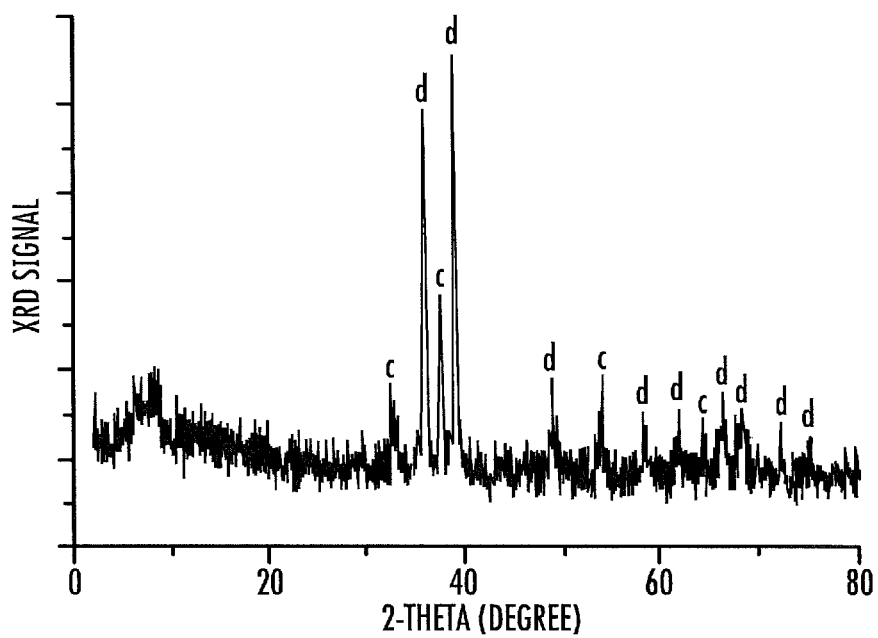
FIG. 11 is a chromatogram of the results of X-ray diffraction analysis of the resulting solid catalyst (composed of CaO and CuO) after the calcination treatment of the spent catalyst (the mixture of $Ca(OH)_2$ and Cu) at 910° C. for three hours.

In experiments to regenerate spent catalyst, sufficient water (calculated based on $Ca(LA)_2$ solubility) was added to the product mixture after reaction. The suspension (Cu and some $Ca(OH)_2$ and/or $CaCO_3$) were in solid phase. The suspension was filtered under vacuum (for over an hour). The filter cake was then collected for calcination. $Ca(OH)_2$ and $CaCO_3$ are readily regenerated to CaO, but it is rather difficult to regenerate Cu to $Cu_2O$ and retain it as $Cu_2O$ throughout the high-temperature calcination process. After the calcination treatment of the spent catalyst (the mixture of $Ca(OH)_2$ and Cu) at 910° C. for three hours, the resulting solid catalyst proved to be composed of CaO and CuO, as depicted in FIG. 11. CaO was evidenced after calcination, which confirmed that the reason that no Ca-compound was shown in FIG. 10A was due to its amorphous form. In FIG. 11, the peaks marked with "c" are the characteristic peaks of CaO, whereas the peaks marked with "d" are the characteristic peaks of CuO.

Therefore, because of its ease of regeneration the catalytic potential of CuO was further investigated. Previously, results (Table 1) showed that the combined use of CaO&CuO did not show good catalytic activity at 190° C.; consequently, experiments were conducted at slightly higher temperatures to investigate whether there was a workable temperature range for CaO&CuO.

Table 3 summarizes glycerol conversion, LA and PG yields, and carbon balance at various temperatures for different time spans when CaO&CuO were used as the catalysts. Glycerol conversion increased with the increase of temperature or reaction time. For a given temperature, no obvious trend was observed for LA yield, while PG seemed to increase gradually as the reaction time extended. In some embodiments, a couple of good conditions are 230° C. for 120 minutes (conversion 86.7%, LA yield 51.7%, and PG yield 30.8%), and 240° C. for 90 minutes (conversion 87.5%, LA yield 54.6%, and PG yield 27.7%). Several other conditions, such as 60, 90 and 180 minutes at 230° C. and 60 minutes at 240° C., were also relatively good. The concept of catalysts regeneration was also proven, and the result was shown in Section B of Table 3. Similar catalytic activity was observed after reusing the catalysts for another two times after regeneration.

TABLE 3

Glycerol conversion, LA yield, PG yield, and carbon balance at different reaction temperatures for various time spans with CaO (0.4 mol per mol glycerol) and CuO (0.08 mol per mol glycerol). Section A used fresh catalysts; Section B used regenerated catalysts.

Section A: Fresh catalysts

| Temperature (° C.) | Reaction time (min) | Conversion (%) | LA yield (%) | PG yield (%) | Carbon balance (%) |
|---|---|---|---|---|---|
| 210 | 60 | 72.8 ± 1.1 | 45.6 ± 1.8 | 21.6 ± 0.7 | 94.4 ± 3.6 [a] |
| 210 | 90 | 77.6 ± 0.1 | 46.6 ± 0.8 | 26.4 ± 0.0 | 95.3 ± 1.0 |
| 210 | 120 | 78.7 ± 1.4 | 42.7 ± 1.1 | 25.1 ± 1.6 | 89.0 ± 4.1 |
| 210 | 180 | 81.8 ± 0.3 | 45.8 ± 0.2 | 28.3 ± 0.1 | 92.3 ± 0.3 |
| 220 | 30 | 66.5 ± 0.1 | 41.2 ± 0.0 | 16.6 ± 0.0 | 91.3 ± 0.2 |
| 220 | 60 | 73.3 ± 3.8 | 44.3 ± 6.0 | 21.6 ± 2.4 | 92.7 ± 11.8 [a] |
| 220 | 90 | 76.6 ± 3.7 | 47.0 ± 1.1 | 21.7 ± 0.5 | 92.0 ± 4.3 |
| 230 | 30 | 77.8 ± 0.1 | 47.6 ± 0.6 | 17.6 ± 0.2 | 87.5 ± 0.9 |
| 230 | 60 | 81.2 ± 1.9 | 52.1 ± 4.0 | 22.2 ± 0.4 | 99.3 ± 0.9 [a] |
| 230 | 90 | 83.7 ± 0.5 | 51.4 ± 1.8 | 26.9 ± 0.9 | 94.6 ± 3.2 |
| 230 | 120 | 86.7 ± 0.1 | 51.7 ± 0.1 | 30.8 ± 3.7 | 95.9 ± 3.7 [a] |
| 230 | 180 | 87.1 ± 0.6 | 51.3 ± 0.2 | 28.3 ± 2.0 | 92.5 ± 2.3 |
| 240 | 60 | 84.4 ± 0.2 | 50.9 ± 0.1 | 24.5 ± 0.5 | 91.0 ± 0.5 |
| 240 | 90 | 87.5 ± 0.6 | 54.6 ± 7.8 | 27.7 ± 0.6 | 94.8 ± 9.0 |

Section B: Regenerated catalysts [b]

| Reuse | Temperature (° C.) | Time (min) | Conversion (%) | LA yield (%) | PG yield (%) | Carbon balance (%) |
|---|---|---|---|---|---|---|
| Fresh | 230 | 120 | 86.7 | 51.7 | 30.8 | 95.9 |
| 1st time | 230 | 120 | 83.5 | 49.3 | 28.4 | 94.2 |
| 2nd time | 230 | 120 | 86.3 | 50.6 | 29.7 | 94.0 |
| Fresh | 210 | 60 | 72.8 | 45.6 | 21.6 | 94.4 |
| 1st time | 210 | 60 | 73.5 | 45.8 | 22.9 | 95.2 |
| 2nd time | 210 | 60 | 72.0 | 45.1 | 22.1 | 95.2 |

[a] Data with the subscription "a" were calculated based on two independent runs with two samples for each run; the data for the rest of the conditions were calculated based on two samples from a single run.

[b] The catalyst regeneration was conducted in the following manner. The mixture after reaction was washed out with enough amount of water calculated based on $Ca(LA)_2$ solubility. Sonication was applied to the suspended solution to thoroughly dissolve residual organic products and unreacted glycerol off the surface of spent catalysts. Filtration was then conducted to collect the solid particles; the filter cake was rinsed several times with DI water, and then collected and calcinied in the air at 910° C. for three hours. The calcined solid (usually in clumps) needs to be ground to fine power. It was assumed that CuO could be totally regenerated (this assumption was supported by our results). However, since part of Ca in the form of $Ca(LA)_2$ was washed into filtrate, CaO catalyst was not fully regenerated and Ca content in the regenerated catalyst mixture needs to be analyzed, so that the right amount of CaO could be added to make up to the desired CaO/CuO ratio. To determine the Ca content, a portion of the regenerated solid was sampled and added into a $H_2SO_4$ solution. CaO reacted with $H_2SO_4$ to form $CaSO_4$ (insoluble), and CuO reacted with $H_2SO_4$, forming $CuSO_4$ (soluble). The precipitate ($CaSO_4$) was collected, dried, weighed and backed calculated to CaO.

Figure 12:
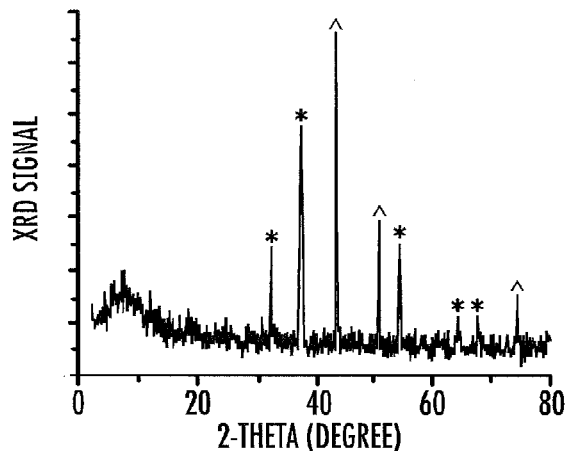
FIG. 12 is a chromatogram of the results of X-ray diffraction analysis of spent catalyst after calcinations at 910° C. in a $N_2$ atmosphere for three hours.

Theoretically, when the spent catalyst (a mixture of $Ca(OH)_2$ and Cu) is calcined in $N_2$ atmosphere at 910° C., the resulting solid catalyst should be composed of CaO and Cu. The verified result is shown in FIG. 12, showing characteristic peaks of CaO and Cu (the peaks marked with "*" are the characteristic peaks of CaO, whereas the peaks marked with "^" are the characteristic peaks of Cu). Therefore, replacing $Cu_2O$ or CuO with Cu was also explored. The previous results presented herein showed that CaO&Cu did not provide good catalytic activity at 190° C. (Table 1); therefore, experiments were conducted at higher temperatures for Cu&CaO.

Table 4 summarizes glycerol conversion, LA and PG yields, and carbon balance at various temperatures when Cu&CaO (0.08 mol Cu per mol glycerol mix with 0.4 mol CaO per mol glycerol) were used as the solid catalysts. Refined glycerol (100 wt %) was used for all the experiments. Copper activated the reaction at an even higher temperature range, compared to CuO. Although LA yield did not show significant decrease, PG yields were lower compared to the PG yields that were achieved with CuO or $Cu_2O$. Considering these factors, Cu did not seem to be a desirable choice, and no regeneration attempt was expended.

TABLE 4

Glycerol conversion, LA yield, PG yield, and carbon balance at different reaction temperatures for various time spans with CaO (0.4 mol per mol glycerol) and Cu (0.08 mol per mol glycerol).

| Temperature (° C.) | Reaction time (min) | Conversion (%) | LA yield (%) | PG yield (%) | Carbon balance (%) |
|---|---|---|---|---|---|
| 210 | 60 | 23.5 ± 3.3 | 19.2 ± 0.5 | 4.6 ± 0.8 | 100.3 ± 2.0 |
| 210 | 90 | 29.1 ± 6.4 | 20.2 ± 1.0 | 4.7 ± 0.5 | 95.9 ± 6.8 |

TABLE 4-continued

Glycerol conversion, LA yield, PG yield, and carbon balance at different reaction temperatures for various time spans with CaO (0.4 mol per mol glycerol) and Cu (0.08 mol per mol glycerol).

| Temperature (° C.) | Reaction time (min) | Conversion (%) | LA yield (%) | PG yield (%) | Carbon balance (%) |
|---|---|---|---|---|---|
| 210 | 120 | 30.1 ± 0.6 | 25.4 ± 0.4 | 5.4 ± 0.0 | 100.7 ± 1.0 |
| 230 | 60 | 43.4 ± 5.2 | 40.9 ± 0.1 | 9.3 ± 1.2 | 106.8 ± 3.9 |
| 230 | 90 | 52.7 ± 0.6 | 44.3 ± 0.3 | 10.2 ± 1.8 | 101.8 ± 2.1 |
| 250 | 60 | 69.2 ± 2.2 | 49.0 ± 1.5 | 11.3 ± 0.5 | 91.1 ± 3.2 [a] |
| 250 | 90 | 72.9 ± 0.6 | 53.1 ± 14.2 | 14.2 ± 1.1 | 94.5 ± 0.6 |
| 260 | 75 | 71.0 ± 0.3 | 45.2 ± 0.5 | 14.2 ± 0.1 | 88.3 ± 0.9 |
| 260 | 90 | 74.3 ± 0.9 | 44.5 ± 2.0 | 14.2 ± 1.0 | 84.4 ± 2.2 [a] |
| 260 | 120 | 81.0 ± 1.0 | 43.7 ± 1.3 | 16.1 ± 0.8 | 80.3 ± 2.8 |
| 270 | 60 | 75.6 ± 0.6 | 48.3 ± 1.4 | 14.3 ± 0.3 | 87.0 ± 2.4 |
| 270 | 90 | 80.0 ± 1.3 | 45.7 ± 2.0 | 15.5 ± 2.3 | 81.2 ± 4.2 [a] |
| 270 | 120 | 83.0 ± 0.3 | 51.6 ± 0.6 | 13.5 ± 0.3 | 82.1 ± 1.2 |

[a] Data with the subscription "a" were calculated based on two independent runs with two samples for each run; data for the rest of the conditions were calculated based on two samples from a single run.

Figure 13:
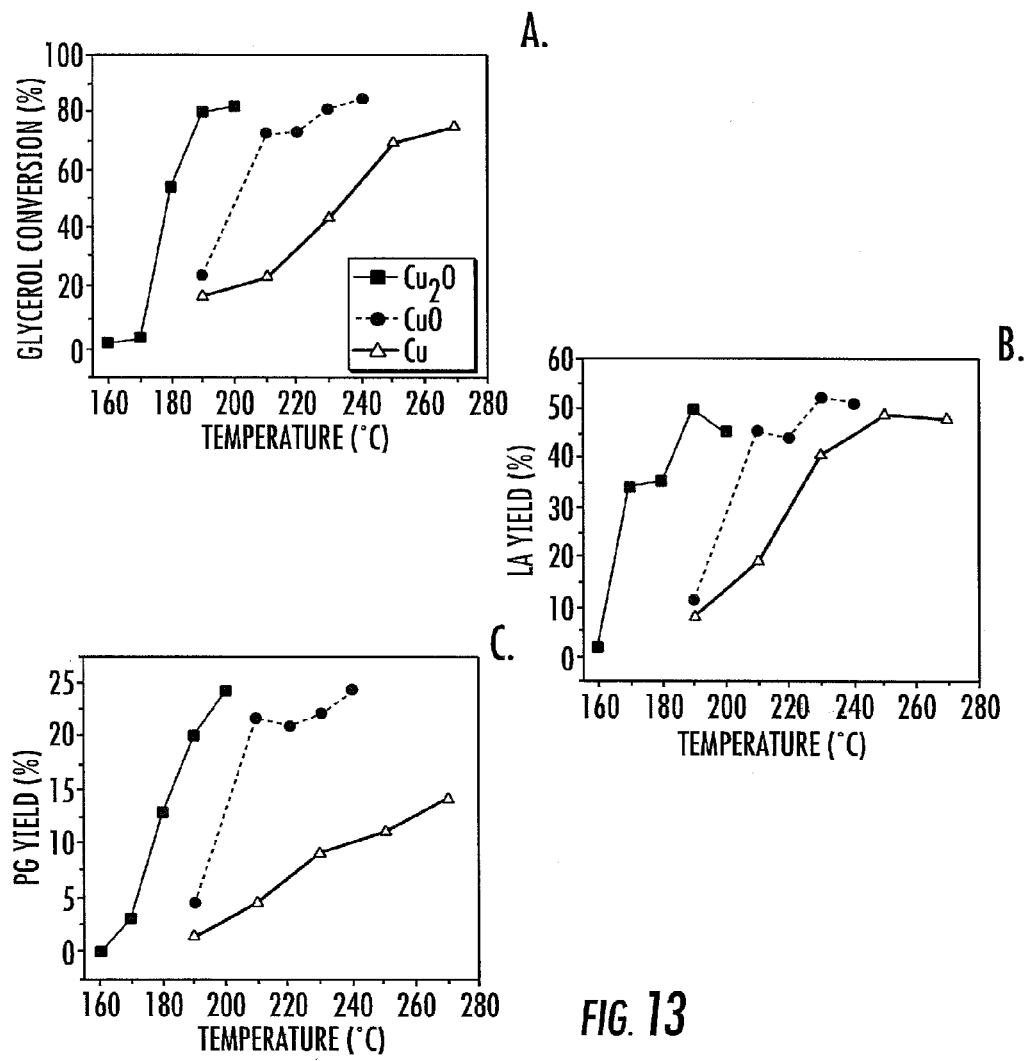
FIGS. 13A-13C are graphical depictions comparing the catalysts Cu, $Cu_2O$ and CuO and their effects on glycerol conversion (FIG. 13A), lactic acid yield (FIG. 13B), and propylene glycol yield (FIG. 13C)

The results clearly show the catalytic activity descending in the sequence of $Cu_2O > CuO > Cu$. The best result with $Cu_2O$ was 79.55% conversion, 48.24% LA yield and 21.09% PG yield at 190° C. for 60 minutes. The best result with CuO occurred at 240° C. after 90 minutes, resulting in 87.5% glycerol conversion, 54.5% LA yield, and 27.7% PG yield. For Cu&CaO, the best result achieved was 72.9% glycerol conversion (FIG. 13A), 53.1% LA yield (FIG. 13B), and 14.2% PG yield (FIG. 13C) at 250° C. for 90 minutes. Nevertheless, all the three copper catalysts showed consistent trend in response to temperature and reaction time length. Glycerol conversion increased as the reaction temperature increased or as the reaction time extended. In general, a slight increase trend was observed for PG yield with the increase of reaction time at a given temperature; but no clear trend in LA yield was observed in term of the time factor. For a given reaction time (e.g. 60 minutes, FIGS. 13A-13C), LA yield did not keep increasing with the increase of temperature, and thus a maximum could be identified. On the contrary, PG yield seemed to continue increasing with the increasing temperature (valid for at least the investigated temperature ranges). Cu activated the reaction at higher temperature range than $Cu_2O$ and CuO, and the reaction was slower, too. Furthermore, compared to using $Cu_2O$ and CuO, the yields of PG were significantly lower when Cu was used. Therefore, Cu did not seem to be a desirable choice considering these factors. For a clear presentation of some trends that were found, the data from FIG. 6, and Tables 3 and 4, was extracted and the results of the 60-min reactions plotted at various temperatures for $Cu_2O$, CuO and Cu (FIGS. 13A-13C).

An advantage of the disclosed methods is the improvement of the LA productivity, which saves operating cost of the production plant and ultimately leads to more profits. In some existing methods excessive corrosion of a reactor can be detrimental to glycerol conversion, a problem overcome by the disclosed methods and systems. Furthermore, the disclosed methods result in significant yield of additional high-value product propylene glycol.

Quantification of chiral D- and L-lactic acid was also selectively conducted. As shown in Table 5, there was no significant indication of chiral selectivity for all the catalysts tested; L-LA and D-LA were equally produced.

TABLE 5

Chiral composition of lactic acid produced using different catalysts under different conditions.

| Catalyst | Base-to-glycerol ratio (mol/mol) | $Cu_2O$-to-glycerol ratio (mol/mol) | Reaction condition | LA yield (%) | % of L-LA | % of D-LA | L/D Ratio |
|---|---|---|---|---|---|---|---|
| CaO&$Cu_2O$ | 0.4 | 0.04 | 190° C., 60 min | 48.2 | 50.0[a] | 50.0 | 1.000 |
| CaO&$Cu_2O$ | 0.4 | 0.04 | 180° C., 60 min | 30.7 | 49.9 | 50.1 | 0.997 |
| CaO&$Cu_2O$ | 0.4 | 0.04 | 270° C., 60 min | 19.9 | 49.3 | 50.7 | 0.973 |
| SrO&$Cu_2O$ | 0.2 | 0.04 | 160° C., 60 min | 45.1 | 50.0 | 50.0 | 1.000 |
| $Cu_2O$-on-CaO | 0.332 | 0.066 | 190° C., 60 min | 52.4 | 50.5 | 49.5 | 1.022 |
| $Cu_2O$-on-CaO | 0.4 | 0.04 | 190° C., 60 min | 52.5 | 49.8 | 50.2 | 0.993 |
| $Cu_2O$-on-CaO | 0.445 | 0.022 | 190° C., 60 min | 41.0 | 50.4 | 49.6 | 1.017 |

[a] calculated from two samples from two individual reaction runs.

Example 9

Discussion Regarding the Reaction Network

Multiple reactions occur during the glycerol conversion process with solid alkaline earth metal oxides, some of which are summarized in Equations 1-5 (see below). Equations 1 and 2 describe the overall equations for glycerol conversion to LA and PG, respectively. During the reaction process, hydrogen generated from LA formation is used in-situ in the conversion of glycerol to PG. Released in situ, $H_2$ molecules instantaneously have good contact with the active centers on the copper catalyst and adsorbed glycerol, minimizing the adsorption process to catalyst surface. Meanwhile, CuO (Equation 4) or $Cu_2O$ (Equation 5) is gradually reduced to Cu, which is less catalytically active for dehydrogenation. The reaction rate decreases due to this reduction of copper catalysts (e.g. $Cu_2O$ was reduced to Cu during the reaction course); continuous consumption of CaO and the reactant also accounts for the decrease in the reaction rate of LA and PG formation.

$$2C_3H_8O_3 + CaO \rightarrow Ca(C_3H_5O_3)_2 + 2H_2 + H_2O \qquad \text{Equation 1}$$

(Ca can be replaced by Sr or Mg, depending on which alkaline earth metal oxide was used)

$$C_3H_8O_3 + H_2 \rightarrow C_3H_8O_2 + H_2O \qquad \text{Equation 2}$$

$$CaO + H_2O \rightarrow Ca(OH)_2 \qquad \text{Equation 3}$$

(Ca can be replaced by Sr or Mg, depending on which alkaline earth metal oxide was used)

$$CuO + H_2 \rightarrow Cu + H_2O \qquad \text{Equation 4}$$

$$Cu_2O + H_2 \rightarrow 2Cu + H_2O \qquad \text{Equation 5}$$

FIG. 1 shows the proposed reaction pathway to the two major products, LA and PG, from the conversion of glycerol 30. The entire process initiates with the conversion of glycerol 30 to glyceraldehyde 34 via glyceroxide ion 32. Each of CaO and Cu-catalyst plays an important role: CaO advances the formation of glyceroxide ion, while Cu-catalyst promotes the hydrogen abstraction. In a basic condition, glyceraldehyde 34 is converted to 2-hydroxypropenal 36, which readily converts to pyruvaldehyde 38 via keto-enol tautomerization (no catalyst is necessary in this step). Hydrogen addition can occur to both 2-hydroxypropenal 36 and pyruvaldehyde 38, and PG 42 is formed as the result; Cu-catalyst is indispensable for this step. Pyruvaldehyde 38 can also undergo benzilic acid rearrangement with the assistance of CaO, and calcium lactate 40 is formed down this path.

Such a scheme can help to explain the experimental data in response to different Cu-catalysts. The dehydrogenation capability descended in the order of $Cu_2O>CuO>Cu$, which caused the difference in the workable temperature range among these Cu-catalysts ($T_{Cu_2O}<T_{CuO}<T_{Cu}$, where T is the reaction temperature). Copper might also have less catalytic activity than CuO and $Cu_2O$ in hydrogenation (36/38 to 42). This could have resulted in that higher percentage of 2-hydroxypropenal 36/pyruvaldehyde 38 took the path of benzilic acid rearrangement, which was a parallel competition to the formation of PG 42. Therefore, PG 42 yields ever reached with Cu (in Cu's workable temperature range) were systematically lower compared to those with either CuO or $Cu_2O$ (refer to FIG. 1). The attraction of solid base to protons helps the formation of glyceroxide ion 32. The stronger basicity is the alkaline earth metal oxide, the more efficient attraction is to H in the hydroxyl group and the easier, to form glyceroxide ion 32. Not wishing to be bound by any particular theory, this appears to explain why the observed catalytic activity follows the order of SrO>CaO>MgO. Similarly, with more available basic sites, more glyceroxide ions 32 are readily formed. Not wishing to be bound by any particular theory, this appears to explain the glycerol 30 conversion increase with the increase of CaO dosage at a given temperature.

Figure 14:
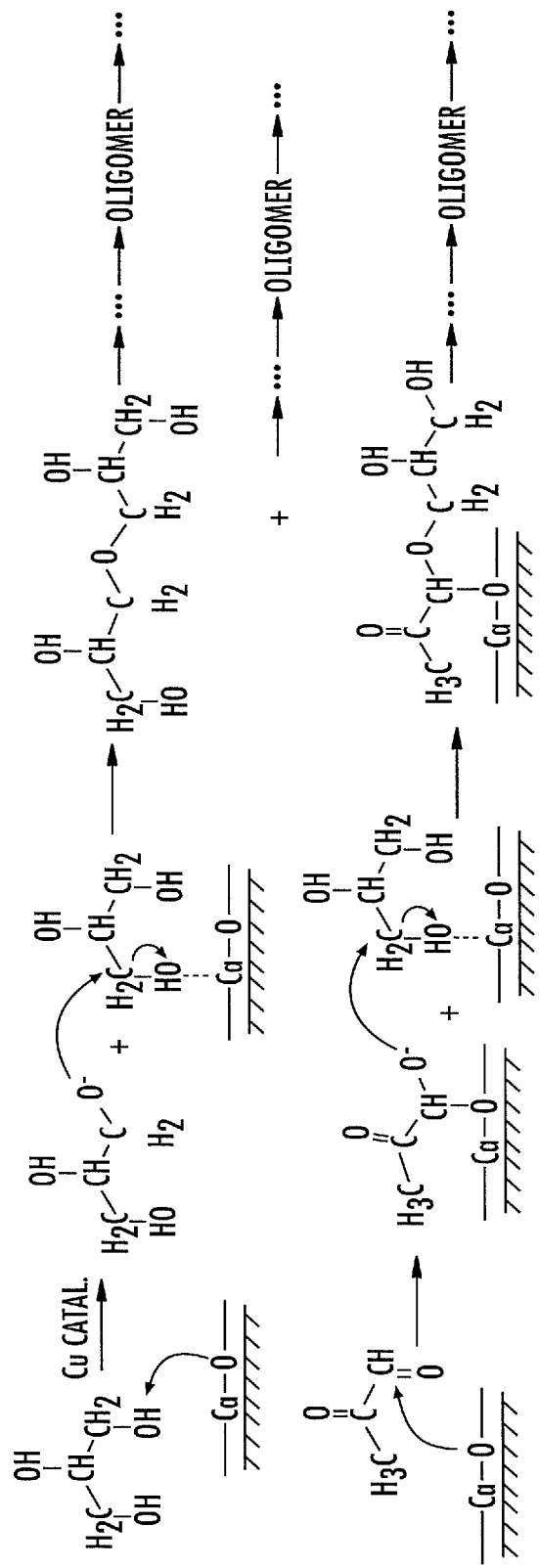
FIG. 14 is a chemical pathway schematic depicting the reaction mechanism of oligomerization/polymerization.

Unfortunately, base-assisted formation of glyceroxide ion can also branch into oligomerization. Furthermore, instead of benzilic acid arrangement (intramolecular reaction), pyruvaldehyde can also undergo intermolecular reaction, leading to higher molecular weight chemicals. Examples of oligomerization/polymerization are illustrated in FIG. 14. These reactions can lead to solid (or water-insoluble) products deposited on solid catalysts, which can in some instances contribute to the loss of carbon balance.

Example 10

Analysis of the Direct Use of Crude Glycerol

Figure 15:
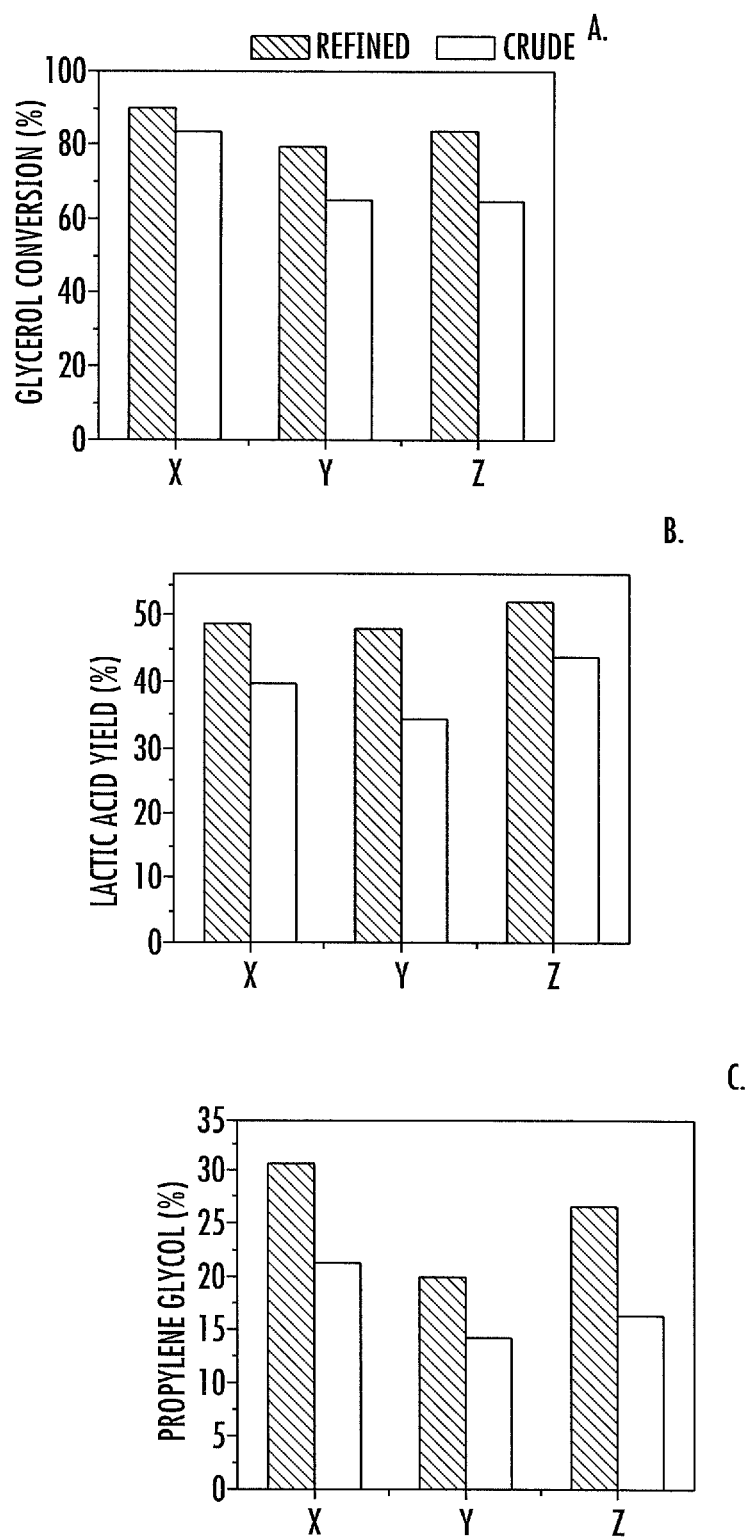
FIGS. 15A-15C are histograms comparing refined glycerol and crude glycerol and the effects on glycerol conversion (FIG. 15A), lactic acid yield (FIG. 15B), and propylene glycol yield (FIG. 15C)

In some embodiments a crude glycerol sample can contain about 80.12 wt. % glycerol and about 11.41 wt. % water with a pH value of 6.33. FIGS. 15A-15C comparatively shows the reaction results obtained with refined glycerol versus crude glycerol for three different cases (X: $Cu_2O$-on-CaO, CaO:glycerol=0.4 mol/mol, $Cu_2O$:glycerol=0.04 mol/mol, 190° C., 60 min; Y: CaO&$Cu_2O$, CaO:glycerol=0.4 mol/mol, $Cu_2O$:glycerol=0.04 mol/mol, 190° C., 60 min; Z: CaO&CuO, CaO:glycerol=0.4 mol/mol, CuO:glycerol=0.08 mol/mol, 230° C., 90 min.). With the same dosage of catalysts, the glycerol conversion (FIG. 15A), LA (FIG. 15B) and PG (FIG. 15C) yields were all lower when crude glycerol was used as the feedstock, compared to using the refined glycerol. Without being limited by any particular theory or mechanism of action, one reason that could account for the performance downgrade is the acidity of the crude glycerol sample, since CaO was partially consumed by the acid in the crude glycerol sample as a consequence, thereby reducing catalytic capability. Acid addition is a common step adopted by biodiesel producers during crude glycerol refining. The purposes of acid treatment are to neutralize the product and to facilitate soap removal and make high-grade crude glycerol. Since glycerol-to-LA&PG is sensitive to acid, the results disclosed herein suggest that acid treatment in the glycerol-refining process needs to be better controlled, if the crude glycerol is to be dedicated to lactic acid production.

Figure 16:
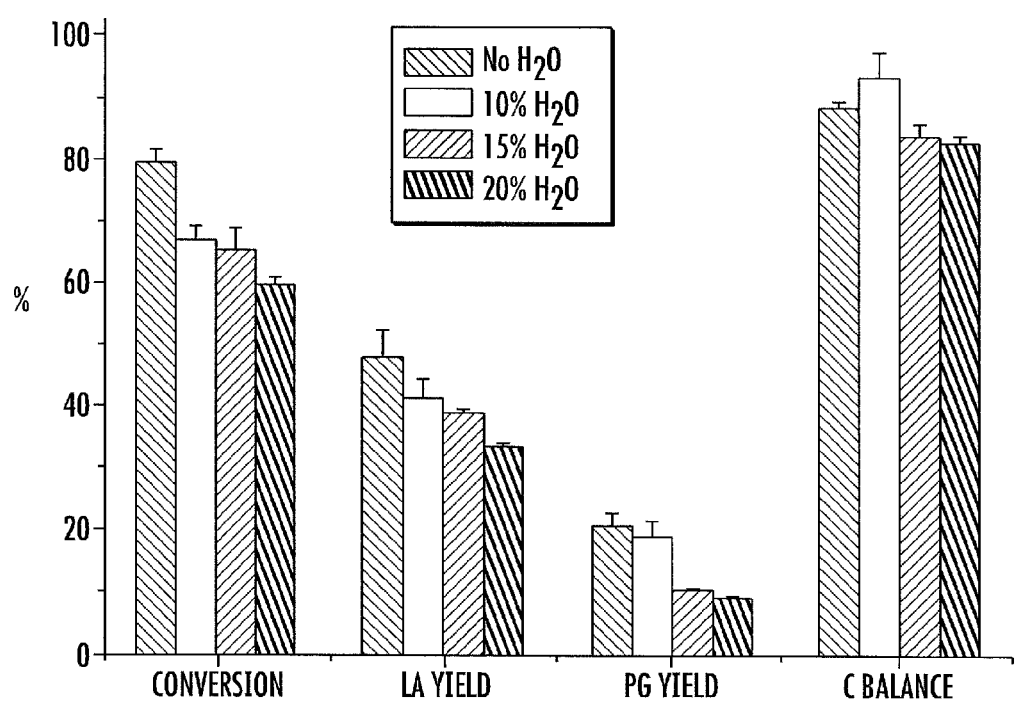
FIG. 16 is a histogram showing the effect of water concentration in crude glycerol on glycerol conversion, lactic acid yield, and propylene glycol yield, and carbon balance.

It was considered that the presence of water in crude glycerol (11.41 wt. %) might be another reason that downgraded the catalytic performance. Therefore, the water tolerance of the process was tested with up to 20% water in the glycerol feed. FIG. 16 shows the results in terms of glycerol conversion, LA yield, PG yield and carbon balance with different water addition (Standard errors for 0% were calculated based on two independent runs with two samples for each run. Standard errors for 10% were calculated based on three independent runs with two samples for each run. Standard errors for 15% and 20% were calculated based on two samples in a single run.). The results show that glycerol conversion, LA and PG yields decreased as the water content increased. CaO would convert into $Ca(OH)_2$ in water, and the basicity of $Ca(OH)_2$ was not as strong as CaO. Therefore, the catalytic activity decreased, resulting in less glycerol conversion. There was still some excessive water in the reactant mix. Partially dissolved $Ca(OH)_2$ catalyzed the reaction via $OH^-$, compensating the activity loss caused by converting CaO to $Ca(OH)_2$. The solubility of $Ca(OH)_2$ is limited, so the concentration of $OH^-$ did not increase with further increase of water content. Concentration of the reactant glycerol decreased with the further increase of water content, resulting in continuous decreases in the reaction rate. More water molecules in the systems hindered the contacts between the reactants/intermediate and the catalyst, especially $H_2$ which has very low solubility in water. Not wishing to be bound by any particular theory, this explains why water was one cause to the less satisfying results when crude glycerol was used.

In an attempt to seek an alternative protocol using heterogeneous catalysis that can tolerate water in glycerol feed, it was discovered that higher LA yields could be achieved with higher dosages of CaO and CuO (Table 6). Over 70% LA yield was achieved with approximately 95% glycerol conversion. Not only the LA yields were significantly increased in general, but also the selectivities to LA were significantly higher as compared to the above result. For all the conditions reported in Table 6, CaO was completely converted to $Ca(OH)_2$ based on stoichiometric relation. Therefore, $Ca(OH)_2$ was the active base ingredient in the system. The solubility of $Ca(OH)_2$ is 0.071 g/100 g water at 100° C., and it would be significantly lower at 190° C. Therefore, most of $Ca(OH)_2$ existed in the solid form, which functioned as the solid catalyst. Higher dosage of $Ca(OH)_2$ was required to compensate its lower basicity compared to CaO. The existence of water molecule hindered the contact of hydrogen and 2-hydroxypropenal/pyruvaldehyde (since $H_2$ has very low solubility in water), resulting in limited PG yields and also allowing more 2-hydroxypropenal/pyruvaldehyde to take the path of LA formation. Table 7 shows that LA yield was influenced by both CaO and CuO, while PG yield was primarily influenced by CuO.

Example 11

Example Industrial Processes and Economic Analysis

Based on the results of the above described studies, a representative industrial process was designed and is disclosed herein for creating LA and/or PG production from glycerol with heterogeneous catalysts, e.g. CaO&CuO. FIG. 2 depicts a flow diagram of a process design for LA and/or PG production from glycerol. FIG. 3 depicts a system design for LA and/or PG production from glycerol (designed in SuperPro Designer). The designed process incorporates glycerol conversion, product separation, and regeneration of catalysts.

In some embodiments, a glycerol conversion process 50 can comprise steps as depicted in FIG. 2. Glycerol 52, CaO 54 and CuO 56 can be reacted in reaction 58 under the conditions disclosed herein. The products 60 of reaction 58 can be cooled and washed with water 62, and the filtrate 70, containing $Ca(LA)_2$, glycerol and PG, can be separated 64 from the filter cake 66 (containing Cu and $Ca(OH)_2$). Filter cake 66 (containing Cu and $Ca(OH)_2$) can be calcinated 68, after which CuO and a portion of CaO (the rest of CaO is lost in the form of $CaSO_4$ 86; see below) can be recycled back to the beginning of glycerol conversion 50. The filtrate 70 can be fed into a crystallizer 72 where $Ca(LA)_2$ 74 can be precipitated out. $Ca(LA)_2$ 74 can be treated with sulfuric acid solution 76 to be converted via reaction 78 to free lactic acid and $CaSO_4$ 80. The formed $CaSO_4$ 86 in solid phase is separated 82 from the aqueous phase in a rotary vacuum filter 82. Lactic acid solution 84 is then concentrated to 90% concentration as final product in a distillation tower. Glyc-

TABLE 6

Reaction results using refined glycerol diluted with water. Reaction was conducted at 230° C. for 60 minutes.

| Water (wt. %) | CaO:GLY mol/mol | CuO:GLY mol/mol | Time min | Conversion % | LA yield % | PG yield % | Carbon balance % |
| --- | --- | --- | --- | --- | --- | --- | --- |
| 50% | 1 | 0.1 | 60 | 66.5 ± 4.8 | 49.7 ± 0.1 | 13.2 ± 5.3 | 96.4 ± 5.3 |
| 33.3% | 1 | 0.05 | 60 | 59.2 ± 4.2 | 44.8 ± 0.8 | 10.6 ± 0.1 | 96.3 ± 3.5 |
| 33.3% | 1 | 0.1 | 60 | 88.4 ± 1.8 | 66.3 ± 6.1 | 13.8 ± 0.4 | 91.7 ± 7.5 |
| 33.3% | 1 | 0.2 | 60 | 94.9 ± 1.7 | 70.2 ± 1.3 | 17.7 ± 2.1 | 93.0 ± 1.8 [a] |
| 33.3% | 0.7 | 0.2 | 60 | 89.3 ± 0.6 | 60.0 ± 2.0 | 17.4 ± 3.0 | 88.2 ± 0.8 [b] |

[a] The data were calculated based on three independent runs with two samples for each run.
[b] The data were calculated based on two independent runs with two samples for each run. The data for the rest of the conditions were calculated based on two samples from a single run.

A desirable condition (highlighted in Table 7) was tested using crude glycerol. The results are shown in Table 7. Similar performance was achieved after tuning the catalyst composition.

TABLE 7

Reaction results using crude glycerol (66.7% crude glycerol and 33.3% water addition). Reactions were conducted at 230° C. for 60 minutes.

| Water addition (wt %) [a] | CaO:GLY (mol/mol) | CuO:GLY (mol/mol) | Conversion % | LA yield % | PG yield % | Carbon balance % |
| --- | --- | --- | --- | --- | --- | --- |
| 33.3% | 1 | 0.2 | 80.7 ± 0.9 [b] | 64.2 ± 5.1 | 10.7 ± 0.1 | 94.2 ± 5.9 |
| 33.3% | 1 | 0.3 | 93.7 ± 2.4 | 69.2 ± 5.6 | 13.7 ± 1.0 | 89.2 ± 8.3 [b] |
| 33.3% | 1.23 | 0.2 | 86.8 ± 1.6 | 63.7 ± 1.2 | 14.6 ± 0.8 | 91.4 ± 1.9 |

[a] Does not include the water in crude glycerol, which is 11.41 wt. %.
[b] The data were calculated based on three independent runs with two samples for each run. The rest of data in the table was based on two independent runs with two samples for each run.

erol, propylene glycerol and $H_2O$ 88 can be further treated in a two-phase distillation process (90 and 94). A first separation/distillation tower 90 can remove water and a second tower 94 can separate glycerol 98 and PG 96. In some embodiments, glycerol 98 can be recycled to be run through the conversion process 50 again.

In some embodiments, a system that converts glycerol to LA and/or PG can comprise a system 100 as depicted in FIG. 3. Referring to FIG. 3, glycerol can be preheated in heater 110 to a desired reaction temperature prior to entering reactor 112. The reaction of glycerol with CaO&CuO can take place in the continuous stirred tank reactor (CSTR) 112. The products can be cooled 114, e.g. in a cooling apparatus, and washed to a rotary vacuum filter 116, where the filtrate, containing $Ca(LA)_2$, glycerol and PG, can be separated from the filter cake (containing Cu and $Ca(OH)_2$). Filter cake can be delivered to a furnace 118 for calcinations. After calcination, CuO and a portion of CaO (the rest of CaO is lost in the form of $CaSO_4$) can be recycled back to glycerol conversion. The filtrate can be fed into a crystallizer 120, where $Ca(LA)_2$ can be precipitated out. $Ca(LA)_2$ can be treated with sulfuric acid solution to be converted to free lactic acid and $CaSO_4$ in reactor 122. The formed $CaSO_4$ is solid phase and can be separated from the aqueous phase in a rotary vacuum filter 124. Lactic acid solution can then be concentrated to 90% concentration as final product in a distillation tower 126. Glycerol and propylene glycol can be separately obtained after two subsequent separation towers, where a first tower 130 removes water and a second tower 132 separates glycerol and PG. The products LA and PG can be stored in containers 128 and 130, respectively, for periodic delivery. In some embodiments, coolers 134, 136 and 138 can provide for liquid condensation. In some embodiments, water used in the method and/or system can be recycled.

For modeling such a production plant, the parameter input for the CSTR was based on one of the desirable conditions achieved in this study for CaO&CuO (230° C. and 90 min). 51.4% LA yield and 26.7% PG yield was used. All the procedures were modeled as a continuous process, which sets up an ultimate goal for the development of this technology. Costs of the raw materials used in the models are listed in Table 8. The worst case scenario was modeled assuming that the price of glycerol feedstock is $800/MT (this is for refined glycerol; crude glycerol with >85% glycerol content could be as low as $180/MT). The designs for different production capabilities (10,000 MT and 100,000 MT) of LA were incorporated. The prices of the refined and crude glycerol were obtained from industry sources. The prices of CaO, CuO, $H_2SO_4$, LA (90%), and PG were obtained from the international trading sources. Other parameters used were designed in the SuperPro Designer software unless otherwise specified. All the numbers were around the median of the listed price range for each specific chemical. Unreacted glycerol and water can be recycled and reused in the process. CuO and partial of CaO can be reused after regeneration; no material loss (in filtration and transportation) was considered during the regeneration process. As a result, these portions of recycled/regenerated materials are listed as "credit" in Table 9, reducing the net cost of raw materials. The net raw material cost for a 10,000 MT plant capacity is $13,366,006, and the net raw material cost for a 100,000 MT plant capacity is $137,475,744. In addition, a significant amount of CaO is converted to $Ca(LA)_2$, which is branched out in the filtrate stream and eventually becomes $CaSO_4$. Therefore, the calculation of these two raw materials took into account these factors. In the modeling, $CaSO_4$ generated during the neutralization step 120 (FIG. 3) as solid waste was considered and assigned $50/MT waste treatment cost. However, depending on the quality of $CaSO_4$, it could be a marketable material (e.g. for dry wall production) and be considered as a credit (~$100/MT). LA and/or PG are the major sources of revenues. In addition, $H_2$ is a value-added product in the gas stream, which can be used for other $H_2$-dependent processes. In our models, $H_2$ was also considered as one contributor to the total revenue.

TABLE 8

Overall material balance, raw material cost, and revenue.

| | Unit cost ($/MT) | Total consumption or production for different annual production (MT) | | Total cost or value ($/year) | |
|---|---|---|---|---|---|
| | | 10,000MT | 100,000MT | 10,000MT | 100,000MT |
| Raw materials | | | | | |
| Glycerol | 800 | 19124 | 191244 | 15299489 | 152994892 |
| CaO | 150 | 4658 | 46583 | 698746 | 6987459 |
| water | 26.5 | 32076 | 320760 | 850014 | 8500140 |
| CuO | 6200 | 1331 | 13307 | 8250260 | 82502596 |
| $H_2SO_4$ (50 wt %) | 108.25 | 10388 | 103867 | 1124498 | 15060657 |
| Total | | | | 26223006 | 266045744 |
| Recycled materials (credit) | | | | | |
| Glycerol | 800 | 4220 | 42202 | 3376000 | 33762000 |
| water | 26.5 | 36879 | 368789 | 977000 | 9772000 |
| CaO&CuO | 2820 | 3019.5 | 30194.9 | 8504000 | 85036000 |
| Total | | | | 12857000 | 128570000 |
| Net cost of raw materials | | | | 13366006 | 137475744 |
| Revenue & Credits | | | | | |
| 90% Lactic acid | 1800 | 10011 | 100103 | 18020000 | 180185000 |
| Propylene glycol | 1900 | 4258 | 42582 | 8091000 | 80906000 |
| $H_2$ | 2700 | 67 | 670 | 181000 | 1808000 |
| Total | | | | 26292000 | 262899000 |

Table 9 shows the relevant information about the costs of the major equipment for the glycerol-to-LA&PG conversion. The installation and maintenance costs are expressed as a multiplier times the purchase cost of that specific equipment. The installation cost varies depending on a specific type of equipment [6]. 15% of the purchase cost (PC) was used as the maintenance/repair cost for the rotary vacuum filter and 10% for the rest of equipment. These percentages fall within the range of 2-20% by chemical engineering economics standard. Some typical labor requirements are used for the process equipment for the 10,000 MT production capacity. In a modern intensive operation, labor is considered as insensitive to the size of equipment.

TABLE 9

The relevant cost information of the major equipment.

| Ref. No. in FIG. 3 | Equipment name | Purchase cost (PC) ($) 10,000MT | Purchase cost (PC) ($) 100,000MT | Installation cost (*PC) | Maintenance cost (*PC) | Labor (labor/equipment/shift) |
|---|---|---|---|---|---|---|
| 112 | CSTR | 1112000 | 2832000 | 0.45 | 0.10 | 0.5 |
| 116 | Rotary vacuum filter | 85000 | 324000 | 0.50 | 0.15 | 0.125 |
| 120 | Crystallizer | 931000 | 8658000 | 0.30 | 0.10 | 0.16 |
| 130 | Distillation Column | 36000 | 174000 | 0.70 | 0.10 | 0.3 |
| 126 | Distillation Column | 13000 | 23000 | 0.70 | 0.10 | 0.3 |
| 132 | Distillation Column | 20000 | 26000 | 0.70 | 0.10 | 0.3 |
| 114, 134, 138, 136 | Cooler | 29000 | 29000 | 0.45 | 0.10 | 0.1 |
| 110 | Heater | 8000 | 30000 | 0.45 | 0.10 | 0.1 |
| 122 | CSTR | 575000 | 814000 | 0.45 | 0.10 | 0.5 |
| 124 | Rotary vacuum filter | 68000 | 324000 | 0.50 | 0.15 | 0.125 |
| 118 | Furnace | 100000 | 170000 | 0.50 | 0.10 | 0.5 |

The following assumptions were used in calculating the capital investment:
construction period of 30 months, startup period of 4 months, and project life of 15 years are assumed; the cost of startup and validation is 5% of direct fixed capital;
a 4% inflation rate is assumed;
a 12% working capital is assumed;
loan periods are 10 years for direct fixed capital (with a 9% interest) and 6 years for working capital, up front R&D and up front royalty (with a 12% interest), respectively;
no income tax was considered; and
adjustment for the cost of the unlisted equipment (such as delivery equipment) was made by assuming that it is 20% of the purchase cost of the listed equipment (FIG. 3 and Table 9), and the installation cost was assumed to 0.5 times of the purchase cost of the unlisted equipment.

The calculated components are listed in Table 10. The percentages of the each component in total capital PC are within the common distribution range [7].

TABLE 10

Components of total fixed capital (TFC).

| | Multiplier of PC | Percentage of TFC | 10,000MT | 100,000MT |
|---|---|---|---|---|
| Direct cost | | | | |
| Equipment Purchase Cost (PC) | | 0.175 | 4252000 | 20595000 |
| Installation | Vary (Table 10) | 0.075 | 1829000 | 8110000 |
| Process Piping | 0.35 | 0.061 | 1488000 | 7208000 |
| Instrumentation | 0.40 | 0.070 | 1701000 | 8238000 |
| Insulation | 0.03 | 0.005 | 128000 | 618000 |
| Electrical | 0.10 | 0.018 | 425000 | 2059000 |
| Buildings | 0.45 | 0.079 | 1913000 | 9268000 |
| Yard Improvement | 0.15 | 0.026 | 638000 | 3089000 |
| Service facilities | 0.40 | 0.070 | 1701000 | 8238000 |
| Indirect cost | | | | |
| Engineering | | 0.149 | 3519000 | 16586000 |
| Construction | | 0.149 | 3519000 | 16586000 |
| Contractor's Fee | | 0.043 | 1056000 | 5057000 |
| Contingency | | 0.087 | 2111000 | 10113000 |

The annual operating cost for the heterogeneously catalyzed glycerol-to-LA process was broken down as a percentage of the total. The net cost of the materials was used for the category of "raw materials". When broken down, the costs for the 10,000 MT/yr capacity process are as follows: 60.82% for raw materials, 14.31% for labor-dependent costs, 13.88% for facility-dependent costs, 9.05% for utilities, and 1.93% for waste treatment. When broken down, the costs for the 100,000 MT/yr capacity process are as follows: 76.69% for raw materials, 1.76% for labor-dependent costs, 8.13% for facility-dependent costs, 11.05% for utilities, and 2.37% for waste treatment. Overall, the raw material cost plays a dominant role in the total operating cost in both heterogeneous models. The percentage of raw material cost weighs heavier for the larger production capacity (100,000 MT/yr) compared to 10,000 MT/yr capacity.

The calculated measures regarding the plant economics are listed in Table 11. Such an estimation was calculated based on the assumption that the reaction performance in terms of conversion and yields remained unchanged when the process was scaled up from laboratory scale, and unaffected by the usage of crude glycerol. Nevertheless, the results showed the promising viability of producing LA and PG from glycerol using our heterogeneous catalysis technology.

TABLE 11

Earning outlook after launching the production for different annual production scales.

|  | 10,000MT | 100,000MT |
|---|---|---|
| Gross Margin | 16.57% | 32.03% |
| Return On Investment | 17.27% | 41.17% |
| Payback Time (years) | 5.79 | 2.43 |

Example 12

Analysis and Conclusions

Methods using solid catalysts to simultaneously produce lactic acid and propylene glycol were developed. Compared to the previous attempts to produce lactic acid from glycerol, the disclosed methods achieved higher productivity while substantially reducing corrosion problems. With respect to the production of propylene glycol from glycerol, the disclosed processes can be independent of external hydrogen supply, thereby saving operation and raw-material costs. Different combinations of catalysts and reaction conditions provide tunable ranges for the yields of lactic acid and propylene glycol. The yields of LA and PG can in some embodiments be optimized in the range of 50%-70% and 17%-30%, respectively, with corresponding glycerol conversion of 87%-95%. The process modeling and economic analysis show the economic viability of the technology developed in the instant disclosure.

In some embodiments, described is a method of simultaneous production of LA and/or PG comprising a reaction of liquid glycerol and a mixture of a dehydration catalyst and a base-modifying solid. In some embodiments, highly concentrated glycerol (such as 70, 75, 80, 85, 90, 95, or 100%) can be used for the maximal productivity because of the relative low corrosiveness of the solid base. In some embodiments, highly concentrated glycerol, i.e., 100% glycerol, can be used for the maximal productivity because of the relative low corrosiveness of the solid base. In other embodiments, hydrogen is generated in-situ and does not require addition of external hydrogen. In some embodiments, the dehydrogenation metal catalysts can be, but are not limited to, Cu, $Cu_2O$, CuO, copper ore or copper chromite. In some embodiments, the base-modifying solid can be, but is not limited to, an alkaline earth metal oxide (e.g. MgO, CaO, and SrO) and/or an alkaline earth metal. In some embodiments, the LA produced is racemic with a molar ratio of L-(+)-lactic acid to D-(−)-lactic acid around 1. In another embodiment, the dehydrogenation catalyst is recoverable and recyclable. In another embodiment, different water percentages in the glycerol stock can be used to tune product composition. In still other embodiments, different starting materials can be used to tune product composition. In other embodiments, different pressures can be used to tune product composition. In another embodiment, crude glycerol can be from biodiesel production. In another embodiment, lactate salt can be separated from product mixture by precipitation or crystallization.

REFERENCES

The references listed below as well as all references cited in the specification are incorporated herein by reference to the extent that they supplement, explain, provide a background for or teach methodology, techniques and/or compositions employed herein.
1. Johnson D T, Taconi K A (2007) The glycerin glut: Options for the value-added conversion of crude glycerol resulting from biodiesel production, Environmental Progress 26:338-348
2. Chiu C-W, Dasari M A, Sutterlin W R, Suppes G J (2006) Removal of residual catalyst from simulated biodiesel's crude glycerol for glycerol hydrogenolysis to propylene glycol, Industrial & Engineering Chemistry Research 45:791-795
3. Werpy T, Petersen G (2004) Top value added chemicals from biomass. Results of Screening for Potential Candidates from Sugars and Synthesis Gas. The Pacific Northwest Laboratory, The National Renewable Energy Laboratory, U.S. Department of Energy, Office of Scientific and Technical Information.
4. He W, Li G, Kong L, Wang H, Huang J, Xu J (2008) Application of hydrothermal reaction in resource recovery of organic wastes, Resources, Conservation and Recycling 52:691-699
5. Viboonchart N (accessed December 2011) "Kingdom to become lactic-acid hub." http://www.nationmultimedia.com/home/2010/04/01/business/Kingdom-to-become-lactic-acid-hub-30126072.html.
6. Peter M S, Timmerhaus K D, West R E (2003) Plant Design and Economics for Chemical Engineers (Fifth Edition). McGraw-Hill Companies Inc.
7. Ulrich G D (1984) A guide to chemical engineering process design and economics John Wiley & Sons, Inc.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method of converting glycerol to lactic acid and propylene glycol, the method comprising:
   providing liquid glycerol;
   providing a heterogeneous catalyst, wherein the heterogeneous catalyst comprises a base ingredient and a dehydrogenation ingredient, wherein the base ingredient comprises an alkaline earth metal oxide selected from the group consisting of magnesium oxide (MgO), calcium oxide (CaO), and strontium oxide (SrO); and
   reacting the liquid glycerol with the heterogeneous catalyst,
   whereby glycerol is simultaneously converted to a product comprising lactic acid and propylene glycol.
2. The method of claim 1, wherein the dehydrogenation ingredient comprises a metal catalyst.
3. The method of claim 2, wherein the metal catalyst is selected from the group consisting of copper (Cu), cuprous oxide ($Cu_2O$), copper oxide (CuO), copper chromite ($Cu_2Cr_2O_5$), barium promoted copper chromite (Ba—$Cu_2Cr_2O_5$) and copper ore.
4. The method of claim 1, wherein the base ingredient and dehydrogenation ingredient of the heterogeneous catalyst are mixed or wherein the dehydrogenation ingredient is supported on the base ingredient.

5. The method of claim 4, wherein the heterogeneous catalyst mixture comprises CaO and $Cu_2O$.

6. The method of claim 4, wherein the base supported dehydrogenation ingredient comprises $Cu_2O$ supported on CaO.

7. The method of claim 1, wherein the glycerol is concentrated glycerol.

8. The method of claim 1, wherein the glycerol is crude glycerol, wherein the crude glycerol comprises about 75% to about 85% glycerol and about 5% to about 15% water, wherein the crude glycerol has a pH of about 6 to about 7.

9. The method of claim 1, wherein the dehydrogenation ingredient is recoverable and can be recycled in the method of converting glycerol to lactic acid and/or propylene glycol.

10. The method of claim 1, wherein the source of glycerol is biodiesel production.

11. The method of claim 1, wherein the molar ratio of the dehydrogenation ingredient to glycerol ranges from about 0.02 to about 0.10 and wherein the molar ratio of the base ingredient to glycerol ranges from about 0.2 to about 0.8.

12. The method of claim 1, further comprising regenerating spent catalyst.

13. A method of converting glycerol to lactic acid and propylene glycol, the method comprising:
providing a glycerol stock;
providing a heterogeneous catalyst, wherein the heterogeneous catalyst comprises a base ingredient and a dehydrogenation ingredient;
reacting the glycerol stock with the heterogeneous catalyst;
cooling and washing the products of the reaction, wherein the products comprise lactate salt, glycerol and propylene glycol;
treating the lactate salt with sulfuric acid solution to form free lactic acid and a sulfate salt;
separating the propylene glycol from the remaining products, whereby glycerol is converted to a lactic acid and propylene glycol; and
regenerating spent catalyst, wherein the spent catalyst comprises $Ca(OH)_2$ and Cu, wherein the regeneration comprises a calcination process, wherein the regenerated catalyst comprise CaO and CuO.

14. The method of claim 13, further comprising a two-phase distillation process to separate glycerol and propylene glycol.

15. The method of claim 13, wherein glycerol remaining after the reaction is recycled a glycerol stock in the method of converting glycerol to lactic acid and propylene glycol.

16. The method of claim 13, wherein the dehydrogenation ingredient comprises a metal catalyst, and wherein the base ingredient comprises an alkaline earth metal.

17. A glycerol conversion system, comprising:
a reactor for reacting stock glycerol with a heterogeneous catalyst, wherein the heterogeneous catalyst comprises a base ingredient and a dehydrogenation ingredient;
a rotary vacuum filter for cooling and washing the products of the reaction in the reactor, optionally wherein a filtrate containing calcium lactate, glycerol and propylene glycol is separated from a filter cake containing Cu and $Ca(OH)_2$;
a crystallizer for filtering out calcium lactate from the filtrate, wherein the calcium lactate is treated with sulfuric acid solution to form lactic acid;
a distillation tower for concentrating lactic acid; and
a series of separation towers for separating glycerol and propylene glycol from the filtrate.

18. The system of claim 17, further comprising a furnace for calcinating Cu and $Ca(OH)_2$ in the filter cake to thereby form CuO and CaO, wherein CuO and CaO are recycled and used in the reactor as the dehydrogenation ingredient and base ingredient, respectively.

19. The system of claim 17, further comprising storage containers for storing the produced lactic acid and propylene glycol.

20. The method of claim 1, wherein the simultaneous production of lactic acid and propylene glycol utilizes hydrogen generated in situ during the conversion of glycerol such that an external hydrogen supply is not needed.

21. The method of claim 13, wherein the simultaneous production of lactic acid and propylene glycol utilizes hydrogen generated in situ during the conversion of glycerol such that an external hydrogen supply is not needed.

22. The method of claim 1, wherein the base ingredient comprises an alkaline earth metal oxide selected from the group consisting of calcium oxide (CaO) and strontium oxide (SrO).

23. The method of claim 1, wherein the yield of lactic acid is about 50 to 70 mol %, wherein the yield of propylene glycol is about 17 to 30 mol %, and the glycerol conversion of about 87 to 95 mol %.

24. The method of claim 13, wherein the yield of lactic acid is about 50 to 70 mol %, wherein the yield of propylene glycol is about 17 to 30 mol %, and the glycerol conversion of about 87 to 95 mol %.

25. The method of claim 12, wherein the spent catalyst comprises $Ca(OH)_2$ and Cu, wherein the regeneration comprises a calcination process, wherein the regenerated catalyst comprise CaO and CuO.

* * * * *